US006878527B1

(12) United States Patent
    Appels et al.

(10) Patent No.: US 6,878,527 B1
(45) Date of Patent: Apr. 12, 2005

(54) MODIFIED PROTEINS

(75) Inventors: Rudi Appels, Aranda (AU); Matthew Morell, Aranda (AU); Frank Bekes, Beecroft (AU); Laszlo Tamas, Budapest (HU)

(73) Assignees: Commonwealth Scientific & Industrial Research Organization, Campbell (AU); Biogemma S.A.S. (FR)

( * ) Notice: Subject to any disclaimer, the term of this patent is extended or adjusted under 35 U.S.C. 154(b) by 0 days.

(21) Appl. No.: 09/743,533

(22) PCT Filed: Jul. 12, 1999

(86) PCT No.: PCT/AU99/00563

§ 371 (c)(1),
(2), (4) Date: Oct. 5, 2001

(87) PCT Pub. No.: WO00/02914

PCT Pub. Date: Jan. 20, 2000

(30) Foreign Application Priority Data

Jul. 10, 1998  (AU) .............................................. PP4604

(51) Int. Cl.[7] .............................................. C12P 21/06
(52) U.S. Cl. .......................... 435/69.1; 424/750; 514/2; 530/300
(58) Field of Search .............................. 530/300; 514/2; 424/750; 435/69.1; 800/320, 320.3

(56) References Cited

FOREIGN PATENT DOCUMENTS

| WO | WO 97/25419 | 7/1997 | |
|---|---|---|---|
| WO | WO 98/07747 | 2/1998 | |
| WO | WO 98/08607 | * 3/1998 | ............. B02B/3/14 |

OTHER PUBLICATIONS

Shimoni et al. "A recombinant protein of two high molecular weight glutenins alters gluten polymer formation in transgenic wheat" 1997, Journal of Biological Chemistry, vol. 272, No: 24, pp. 15488–15495.*

Entwistel et al. "Amber codon suppression: the in vivo and in vitro analysis of two C–hordein genes from barley" 1991, Plant Molecular Biology, vol. 17, No: 6, pp. 1217–1231.*

Alpeter F, et al. "Integration and expression of the high––molecular–weight glutenin subunit 1 Ax1 Gene into wheat" *Nature Biotechnology*, 14: 1155–1170 (1996).

Anderson O D et al, "Construction and expression of a synthetic wheat storage protein gene" *Gene*, 174: 51–58 (. 1996).

Blechi, A., et al., "Engineering Changes in Wheat Flour by Genetic Engineering", *Journal of Plant Physiology*, 152:703–707 (1998).

D'Ovidio, R., "Construction of Novel Wheat High–M, Glutenin Subunit Gene Variability: Modification of the Repetitive Domain and Expression in E.coli", *Journal of Cereal Science*, 25:1–8 (1997).

Blechi, A.E., et al., "Applications of Molecular Biology to Understanding and Improving Wheat Quality", *Proceedings, International Wheat Quality Conference*, J. Steele, et al., Eds., pp. 205–211 (1997).

(Continued)

*Primary Examiner*—Christopher Tate
*Assistant Examiner*—Roy Teller
(74) *Attorney, Agent, or Firm*—Dorsey & Whitney LLP; Richard F. Trecartin; Traci H. Ropp

(57) ABSTRACT

A method for producing a modified glutenin or seed-storage protein, the method comprising adding to the protein an exogenous amino acid domain which confers to the modified protein the ability to bind a ligand or other macromolecule. Wherein the modified protein has an ability to incorporate into gluten, modified glutenin or seed-storage proteins, and uses thereof.

16 Claims, 17 Drawing Sheets

```
                                         M   R   Q   L   N   P   C   S
5'... ATAGAATAC A GCATGC TCC CGGCCG CCATGG CCGCGG GATTGTC ATG AGG CAA CTA AAC CCT TGC AGC....
  SP6 Promoter<|  SphI      EagI    NcoI   SacII       BspHI V   P   Q   Q   A   S   C   I   W   S   M   V   * * *
ANG SEQUENCE....GTC CCC CAA CAA GCT TCA TGC ATA TGG AGT ATG GTC TAG GGATCC
                         HindIII      NdeI                      BamHI GGGTACC GAGCTC GAATTC GCCCTATA... 3'
 KpnI    SacI   EcoRI |> T7 Promoter
```

OTHER PUBLICATIONS

Shimoni, Y., et al., "A Recombinant Protein in Two High Molecular Weight Glutenins Alters Gluten Polymer Formation in Transgenic Wheat", *The Journal of Biological Chemistry*, 272: 15488–15495 (1997).

Aalen, R.B., "The transcript encoding two oleosin isoforms are both present in the aleurone and in the embryo of barley (*Hordeum vulgar*)", *Plant. Mol. Biol.*, 28:583–588 (1995).

Bekes, F., et al., "Mixing Properties as a Measure of Reversible Reduction and Oxidation of Doughs", *Cereal Chemistry*, 71:44–50 (1994).

Bushuk. W., "Interactions in Wheat Doughs", *Interactions: The Keys to Cereal Quality*, R.J. Hamer, R.C. Hoseney, Eds., American Association of Cereal Chemists, Inc., St. Paul, MN, pp. 1–16 (1998).

Chamberlain, D.A., et al., "The use of the Emu promoter with antibiotic and herbicide resistance genes for the selection of transgenic wheat callus and rice plants", *Australian Journal of Plant Physiology*, 21:95–112 (1994).

Ciaffi, M., et al., "The low molecular weight glutenin subunit proteins of primitive wheats. III. The genes from D–genome species", *Theoretical and Applied Genetics*, 98:135–148 (1999).

Dubrell, L., et al., "Interaction of Puroindolines with wheat flour polar lipids determines their foaming properties", *J. Agric. Food Chem.*, 45:108–116 (1997).

Gan, Z., et al., "Gas cell stabilization and gas rentention in wheat bread dough", *Journal of Cereal Science*, 21:215–230 (1995).

Gonzalex De La Pena M. et al. "Expression in *Escherichia coli* of Sin a 1 the major allergen from mustard" *European Journal of Biochemistry* 237: 827–832 (1996).

Huang, A.H.C., "Oleosins and oil bodies in seeds and other organs", *Plant Physiology*, 110:1055–1061 (1996).

Kasarda, D.D., "Glutenin structure in relation to wheat quality", *Wheat is Unique*, Y. Pomeranz, Ed., American Assoc. Cereal Chem., St. Paul, MN, pp. 277–302 (1989).

Kobrehel, K., and Sauvaire, Y., "Particular lipid composition in isolated proteins of durum wheat", *J. Agric. Food Chem.*, 38:1164–1171 (1990).

Le Gal–Coeffet M.F., et al., "Expression in *Aspergilus niger* of the Starch–binding domain of glucoamylase," *Eur. J. Biochem.*, 233:561–567 (1995).

MacRitchie, F., "Physiochemical properties of wheat proteins in relation to functionality", *Adv. Food Nutr. Research*, Academic Press Inc. 36:1–87 (1992).

Morrison, W.R., "Recent progress on the chemistry and functionality of flour lipids", *Wheat end–use properties: Wheat and flour characterization for special end uses*, 131–149, H. Salovaara, Ed., University of Helsinki, Lahti (1989).

Tamas, L. et al., Herterologous expression and dough mixing studies of wild type ad mutatn c hordeins. Journal of Cereal Science, 27: 15–22 (1998).

Weeks, J.T., et al., "Rapid production of multiple independent lines of fertile transgenic wheat (*Triticum aestivum*)", *Plant Physiology* 102:1077–1084 (1993).

Witrzens, B., et al., "Comparison of three selectable marker genes for transformation of wheat by microprojectile bombardment" *Aust. J. Plant Physiology* 25:39–44 (1998).

\* cited by examiner

```
5'...ATAGAATAC A GCATGC TCC CGGCCG CCATGG CCGCGG GATTGTC ATG AGG CAA CTA AAC CCT TGC AGC.....
    SP6 Promoter<|  SphI        EagI   NcoI    SacII          BspHI  M   R   Q   L   N   P   C   S V   P   Q   Q   A   s   C   I   W   S   M   V   ***
ANG SEQUENCE....GTC CCC CAA CAA GCT TCA TGC ATA TGG AGT ATG GTC TAG GGATCC
                            HindIII       NdeI                          BamHI GGGTACC GAGCTC GAATTC GCCCTATA... 3'
 KpnI    SacI   EcoRI |> T7 Promoter
```

Figure 1

```
1
ATGAGGCAACTAAACCCTTGCAGCCAAGAGTTGCAATCACCACAACAATCATATCTGCCG
  M   R   Q   L   N   P  Cys  S   Q   E   L   Q   S   P   Q   Q   S   Y   L   Q

61
CAGCCATATCCACAAAACCCATATCTACCGCAAAAACCATTTCCAGTGCAGCAACCGTTT
  Q   P   Y   P   Q   N   P   Y   L   P   Q   K   P   F   P   V   Q   Q   P   F

121
CACACACCCCAACAATATTTCCCCTATCTACCAGAGGAATTGTTTCCCCAATATCAAATA
  H   T   P   Q   Q   Y   F   P   Y   L   P   E   E   L   F   P   Q   Y   Q   I

181
CCAACCCCCCTACAACCACAACAACCATTCCCCCAACAACCACAACAACCTCTTCCTCGG
  P   T   P   L   Q   P   Q   Q   P   F   P   Q   Q   P   Q   Q   P   L   P   R

241
CCCCAACAACCATTCCCCTGGCAACCACAACAACCATTTCCCCAGCCCCAAGAACCAATT
  P   Q   Q   P   F   P   W   Q   P   Q   Q   P   F   P   Q   P   Q   E   P   I

301
CCCCAGCAACCACAACAACCATTCCCACAGCAACCACAACAACCATTCCCACAGCAACCA
  P   Q   Q   P   Q   Q   P   F   P   Q   Q   P   Q   Q   P   F   P   Q   Q   P

361
CAACAAATAATTTTCCAGCAACCCCAACAATCATACCCTGTGCAACCTCAACAGCCATTT
  Q   Q   I   I   F   Q   Q   P   Q   Q   S   Y   P   V   Q   P   Q   Q   P   F 421                                                                          477
CCTCAACAACCTCAACCAGTCCCCCAACAA GCT TCA TGCATATGGAGTATGGTCTAG
  P   Q   Q   P   Q   P   V   P   Q   Q    A   S   Cys  I   W   S   M   V   ***
```

Figure 3

```
HindIII 1                                                    54
AAGCTTCTACCACTCCCACCGCCGTGGCTGTGACTTTCGATCTGACAGCTACCACCACCTAC
     A  S  T  T  P  T  A  V  A  V  T  F  D  L  T  A  T  T  T  Y 114
GGCGAGAACATCTACCTGGTCGGATCGATCTCTCAGCTGGGTGACTGGGAAACCAGCGAC
  G  E  N  I  Y  L  V  G  S  I  S  Q  L  G  D  W  E  T  S  D 174
GGCATAGCTCTGAGTGCTGACAAGTACACTTCCAGCGACCCGCTCTGGTATGTCACTGTG
  G  I  A  L  S  A  D  K  Y  T  S  S  D  P  L  W  Y  V  T  V 234
ACTCTGCCGGCTGGTGAGTCGTTTGAGTACAAGTTTATCCGCATTGAGAGCGATGACTCC
  T  L  P  A  G  E  S  F  E  Y  K  F  I  R  I  E  S  D  D  S 294
GTGGAGTGGGAGAGTGATCCCAACCGAGAATACACCGTTCCTCAGGCGTGCGGAACGTCG
  V  E  W  E  S  D  P  N  R  E  Y  T  V  P  Q  A  C  G  T  S 321    NdeI
ACCGCGACGGTGACTGACACCTGGCGGTGCATATGG
  T  A  T  V  T  D  T  W  R  C  I  W
```

Figure 4

```
HindIII                                                    57
AAGCTTTCGGCAATGAAGATTGCACCCCATGGATGAGTACTCTGATCACTCCACTCCCAAGC
     A I  G  N  E  D  C  T  P  W  M  S  T  L  I  T  P  L  P  S
CM17 . .  .  .  .  .  .  .  .  T  .  .  .  .  .  .  .  .  .  .

117
TGCCGTGACTATGTGGAACAACAAGCATGTCGCATCGAAACGCCCGGGTCGCCGTACCTC
  C  R  D  Y  V  E  Q  Q  A  C  R  I  E  T  P  G  S  P  Y  L
  .  .  N  .  .  .  E  .  .  .  .  .  .  M  .  .  P  .  .  .

177
GCCAAGCAGCAGTGCTGTGGGGAGCTTGCAAACATTCCGCAGCAGTGCCGATGCCAGGCG
  A  K  Q  Q  C  C  G  E  L  A  N  I  P  Q  Q  C  R  C  Q  A
  .  .  .  E  .  .  E  Q  .  .  .  .  .  .  .  .  .  .  .  .

237
CTGCGCTACTTCATGGGGCCGAAGTCTCGTCCGGATCAGAGCGGCCTCATGGAACTCCCC
  L  R  Y  F  M  G  P  K  S  R  P  D  Q  S  G  L  M  E  L  P
  .  .  .  .  .  .  .  .  .  .  .  .  .  .  .  .  .  .  .  .

297
GGATGCCCTAGGGAGGTGCAGATGGACTTCGTGAGGATACTCGTCACGCCGGGGTACTGC
  G  C  P  R  E  V  Q  M  D  F  V  R  I  L  V  T  P  G  Y  C
  .  .  .  .  .  .  .  N  .  .  P  .  .  .  .  .  .  .  .  .

354
AACTTGACGACCGTTCACAACACTCCGTACTGCCTCGCTATGGAGGAGTCTCAGTGG
  N  L  T  T  V  H  N  T  P  Y  C  L  A  M  E  E  S  Q  W
  .  .  .  .  .  .  .  .  .  .  .  G  .  .  .  .  .  .  .

357    NdeI
AGCTGCATATGG
  S  C  I  W
```

Figure 5

```
HindIII                                                    57
AAGCTTACGATGTTGCTGGCGGGGGTGGTGCTCAACAATGCCCTGTAGAGACAAAGCTAAAT
   A  Y  D  V  A  G  G  G  A  Q  Q  C  P  V  E  T  K  L  N 117
TCATGCAGGAATTACCTGCTAGATCGATGCTCAACGATGAAGGATTTCCCGGTCACCTGG
  S  C  R  N  Y  L  L  D  R  C  S  T  M  K  D  F  P  V  T  W 177
CGTTGGTGGAAATGGTGGAAGGGAGGTTGTCAAGAGCTCCTTGGGGAGTGTTGCAGTCGG
  R  W  W  K  W  W  K  G  G  C  Q  E  L  L  G  E  C  C  S  R 237
CTCGGCCAAATGCCACCGCAATGCCGCTGCAACATCATCCAGGGGTCAATCCAAGGCGAT
  L  G  Q  M  P  P  Q  C  R  C  N  I  I  Q  G  S  I  Q  G  D 297
CTCGGTGGCATCTTCGGATTTCAGCGTGATCGGGCAAGCAAAGTGATACAAGAAGCCAAG
  L  G  G  I  F  G  F  Q  R  D  R  A  S  K  V  I  Q  E  A  K 300
AACCTGCCGCCCAGGTGCAACCAGGGCCCTCCCTGCAACATCCCCGGCACTATTGGCTAT
  N  L  P  P  R  C  N  Q  G  P  P  C  N  I  P  G  T  I  G  Y 363    NdeI
TACTGGTGCATATGG
  Y  W  C  I  W
```

MODIFIED PROTEINS

TECHNICAL FIELD

The present invention is directed generally to producing modified proteins and particularly to producing modified glutenin or seed-storage proteins.

BACKGROUND ART

Wheat storage proteins are classified on the basis of their solubility into two classes. The gliadins are readily soluble in aqueous alcohols and are monomeric proteins with only intramolecular disulphide bonds. The glutenins are present in high molecular weight polymers, stabilised by intermolecular disulfide bonds and are not soluble in aqueous alcohols without reducing agent (Kasarda 1989). These proteins are present in high amount in the endosperm and are considered to act as a store of nitrogen, carbon and sulphur for seed germination.

Glutenins form a continuous proteinaceous network called gluten. The unique physico-chemical properties of gluten determine the ability of wheat dough to be processed into baked goods (bread, biscuits, cakes), pasta noodles and other food products. It is understood that the glutenins, which form crosslinks with each other through disulfide bonds, are the most important molecules producing the viscoelastic properties of wheat flour dough (MacRitchie 1992). The unique position of wheat in bread making is due to the ability of the dough to retain gas on expansion. The gluten accounts for about 10% of the dough, and consists mainly of proteins (70–80%) together with starch and lipids. Starch could be granular and damaged starch. The lipid reserves of wheat are non-polar, structural and endosperm lipids (Gan et al., 1995). Structural lipids are also called polar lipids. The endosperm lipids are divided into non-starch lipids and starch lysophospholipids. The structure and properties of gluten are determined by molecular interactions and it is important that these be understood if the functional properties of gluten are to be manipulated.

A dough results from a large variety of interactions between flour constituents facilitated by water. Starch takes up about 46% of the water and damaged starch contributes significantly to the water absorption. It has been shown that during hydration, proteins exude visible strands or fibrils. Specific proteins of flour are bound to flour lipids (polar) upon addition of water (Morrison 1989).

Dough development is visualised as a re-orientation of glutenin polymers to form a membrane network with viscoelasticity and gas retaining properties. Covalent (disulfide) and noncovalent (hydrogen, hydrophobic and ionic) bonds are involved in formation of a fully developed dough. Interactions are further modified during fermentation, baking and even after baking. The disulphide bonds of flour proteins play a key role in the interactions in dough. The bonds form relatively strong crosslinks within and between polypeptide chains and also stabilise other less energetic bonds. Disulphide bonds provide the required stability for the protein matrix until the loaf structure is set by the gelatinisation of the starch and the thermal denaturation of the proteins during baking. Hydrogen bonds are considerably weaker than covalent bonds, but contribute significantly to the structure of dough. A unique feature is the ability to interchange with other hydrogen bonds, which facilitate reorientation of protein chains and allow for stress relaxation. Hydrophobic bonds result from nonpolar groups of flour constituents. Because these bonds are reversible, they can readily accommodate viscous flow and thereby facilitate mechanical dough development. Ionic bonds play relatively small part in dough structure formation but some specific components have an ionisable part or parts. Therefore ionic bond interactions could be important for the Theological properties (for a review, see Bushuk 1998).

A major limitation to evaluating the contributions of various groups of proteins, and of specific structural features of these molecules, to dough functionality has been the lack of appropriate systems that allow specific proteins to be incorporated and tested within the dough. The situation has recently changed, however, due to two advances. The first is the development of small scale testing equipment (Mixograph, Extensograph) with appropriate procedures for incorporating exogenous proteins, including polymeric glutenins into the dough (Bekes et al., 1994). Advantages of this system are the small amount of proteins required for test and the ability to rapidly test multiple samples produced by, for example, protein engineering. The second recent advance is the development of a reliable transformation system for wheat (Weeks et al., 1993, Witrzens et al., 1998), which allows the modification of storage protein composition by the expression of new proteins with, for instance, designed characteristics.

To alter protein-protein, protein-lipid and protein-starch interactions within the gluten matrix, the present inventors have developed a system which enables the incorporation of new surface active molecules or parts of molecules into the gluten matrix.

DISCLOSURE OF INVENTION

In a first aspect, the present invention consists in a method for producing a modified glutenin or seed-storage protein, the method comprising adding to the protein an exogenous amino acid domain which confers to the modified protein the ability to bind a ligand or other macromolecule, wherein the modified protein has an ability to incorporate into gluten.

In one preferred embodiment, the modified glutenin or seed-storage protein further contains one or more exogenous amino acid residues added to its amino acid sequence, more preferably, the one or more amino acid residues are one or more cysteine residues. Preferably, the one or more cysteine residues are incorporated at one or both ends of the amino acid sequence of the protein. The addition of the one or more cysteines allows the modified proteins to be more easily incorporated into gluten in use. The further modifications to the glutenin or seed-storage proteins produced according to the present invention allow or can assist in the incorporation of that protein into the gluten network for food or industrial use.

The present inventors have found that incorporating exogenous amino acid sequences (domains) from proteins other than glutenins or seed storage proteins into glutenin or seed-storage proteins modifies the general properties of gluten, particularly when the modified proteins are used in a range of food applications.

FIG. 16 provides a schematic of the scheme for identifying transgenes in transformed wheat plants by polymerase chain reaction (PCR). A primer pair straddling the interface between the gene and its promoter (from the gene for the high molecular weight glutenin Bx17 for example) ensures that no false positives are detected arising from the high homology between C hordein and gliadin genes.

The binding domain can be any domain that will bind ligands that may be useful in food preparation or in food compositions. In a preferred form, the binding domain is a ligand capable of binding lipids or starches. The present inventors have found that the lipid-binding domain of the barley oleosin gene, the lipid-binding regions of the wheat CM16 protein, and the starch-binding domain of the glucoamylase from *Aspergillus niger* are particularly suitable for the present invention. It will be appreciated, however, that other natural or modified domains would also be suitable for the present invention.

One glutenin or seed-storage protein that has been modified by the present inventors is the C hordein gene from barley. It will be appreciated, however, that other glutenin or seed-storage proteins may also be modified according to the present invention. In wheat, such glutenin or seed proteins include low molecular weight glutenins, high molecular weight glutenins, gliadins, puroindolines or grain softness proteins (also known as friabilins), or Chloroform/Methanol-soluble proteins. Homologues of these proteins exist in other cereals such as diploid, tetraploid and hexaploid wheats, rye, triticale, barley, oats, rice, sorghum, millet and maize and the genes encoding these proteins may also be modified according to the present invention.

In a second aspect, the present invention consists in a modified glutenin or seed-storage protein having a domain inserted therein which confers to the protein the ability to incorporate into gluten or bind a ligand or other macromolecule.

In one preferred embodiment, the modified glutenin or seed-storage protein is produced by the method according to the first aspect of the present invention.

In another preferred embodiment, the modified glutenin or seed-storage protein is ANG/SBD/Cys7Cys236, ANG/OHBD/Cys7Cys236 or ANG/CM16/Cys7Cys236.

In a third aspect, the present invention consists in an isolated nucleic acid molecule encoding a modified glutenin or seed-storage protein according to the second aspect of the present invention.

In a fourth aspect, the present invention consists in an isolated nucleic acid molecule according to the third aspect of the present invention incorporated into a cell such that on expression of the nucleic acid molecule, the cell produces the modified glutenin or seed-storage protein.

The cell may be a recombinant bacterial cell, for example, which is capable of producing the modified glutenin or seed-storage protein. Preferably the bacterial cell is *Escherichia coli*. Alternatively, the cell may be a yeast such as *Pichia* sp. or *Saccharomyces cerevisiae*, an insect cell using an expression system such as the baculovirus expression system, or a mammalian cell. Alternatively, the cell may be a plant cell of a recombinant plant which is capable of producing the modified glutenin or seed-storage protein in the plant's seeds. Preferably the plant cell is a recombinant wheat cell.

In fifth aspect, the present invention consists in the use of a modified glutenin or seed-storage protein according to the second aspect of the present invention in the preparation of a food product.

Examples of food products include leavened or unleavened breads, pasta, noodles, breakfast cereals, snack foods, cakes, pastries or other foods containing flour-based sauces or ingredients.

The modified glutenin or seed-storage proteins according to the present invention, in use, are capable of modifying the structure of doughs and other materials containing gluten in ways which add value and utility to the resultant product. The modified glutenin or seed-storage proteins are suitable for use in the food industry as modifiers of food properties.

The present inventors have shown that modified proteins according to the present invention can be produced in bacterial fermentation and that large scale production of the proteins for commercial use is possible.

In sixth aspect, the present invention consists in the use of a modified glutenin or seed-storage protein according to the second aspect of the present invention in the preparation of a non-food product.

Examples of non-food products include, but not limited to, films, coatings, adhesives, building materials or packaging materials. It will be appreciated that the modified proteins according to the present invention would have the same non-food uses as for normal glutenin or seed-storage proteins.

In a seventh aspect, the present invention consists in the use of a grain or part of a grain containing a modified glutenin or seed-storage protein according to the second aspect of the present invention in the preparation of a food product.

It will be appreciated that the modified glutenin or seed-storage proteins according to the present invention may be contained in, or produced by, a transgenic plant produced by the fourth aspect of the present invention. Thus, the grain or other plant products produced by these plants may be used in the crude form of flour, semolina, bran, pollard, germ fraction, or the like. Such plants may produce a mixture of normal and modified glutenin or seed-storage proteins which can also be used. Mixtures of modified glutenin or seed-storage proteins and other plant-based materials can also be prepared to form improved gluten.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and drawings.

BRIEF DESCRIPTION OF DRAWINGS

FIG. 1: Sequence of the pJANGΔCys7Cys236 vector (SEQ ID NO: 14 and SEQ ID NO: 15). Restriction sites and enzymes of the MCS of pJKKm and pGEM-T plasmids are written in bold. Cloning sites for gene insertion into ANG are underlined and written in bold. Cleavage sites for sub-cloning the gene into pET 11d expression vector are underlined.

FIG. 3: Nucleotide (SEQ ID NO: 18) and amino acid sequence (SEQ ID NO: 19) of ANGΔCys7Cys236 (molecular mass 18.5 kDa) Cysteine residues are marked with bold letters. Extra two amino acids and six nucleotides are written with smaller letters.

FIG. 4: Nucleotide (SEQ ID NO: 20) and amino acid sequence (SEQ ID NO: 21) of the starch binding domain of 1,4-α-D-glucan glucohydrolase from *Aspergillus niger* (molecular mass 11.9 kDa). Small letters are indicating extra nucleotides for cloning and amino acids from ANG molecule. Restriction sites are in bold and underlined.

FIG. 5: Nucleotide (SEQ ID NO: 22) and amino acid sequences of CM16 (SEQ ID NO: 23) and CM17 (SEQ ID NO: 24) (molecular mass is 13.4 kDa). Small letters are indicating extra nucleotides for cloning and amino acids from ANG molecule. Restriction sites are in bold and underlined. First amino acid sequence under the nucleotide sequence represents the CM16 protein, while only differences are shown in CM17 protein.

FIG. 6: Nucleotide (SEQ ID NO: 25) and amino acid sequence (SEQ ID NO: 26) of Puroindoline A (molecular mass is 14.3 kDa). Small letters are indicating extra nucleotides for cloning and amino acids from ANG molecule. Restriction sites are in bold and underlined.

Panel A=SDS-PAGE of fractions from AD494(DE3)/pET-SBD.
Panel B=native PAGE of fractions from AD494(DE3)/pET-SBD.
Panel C=SDS-PAGE of fractions from AD494(DE3)/pET11d.
Panel D=native PAGE of fractions from AD494(DE3)/pET11d.
Lane M=molecular mass markers with masses indicated in kDa.
Lane 1=the unbound flow-through from column loading.

Lanes 2–5=four 5 ml washes with column buffer (50 mM Tris-Cl pH 7.5, 100 mM NaCl , 40 mM dithiothreitol, 1 mM EDTA).

Lanes 6–10=five 5 ml elutions with column buffer containing 15 mM β-cyclodextrin.

Figure 15:
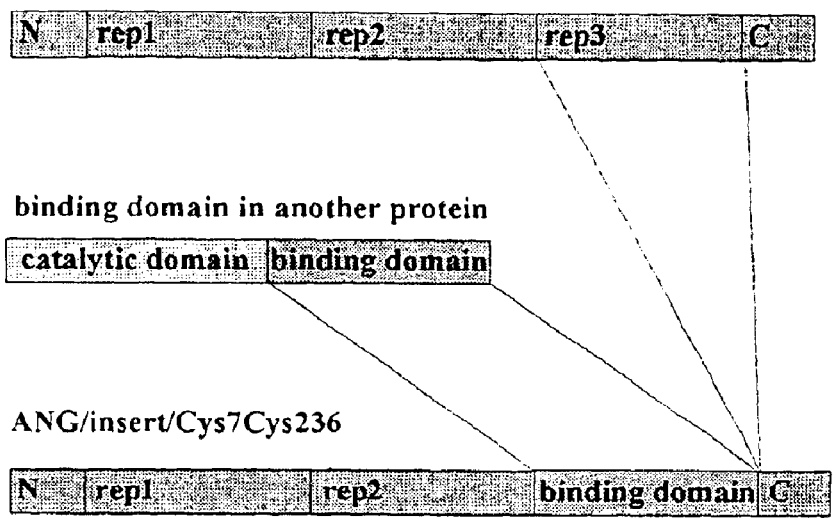
Figure 16:
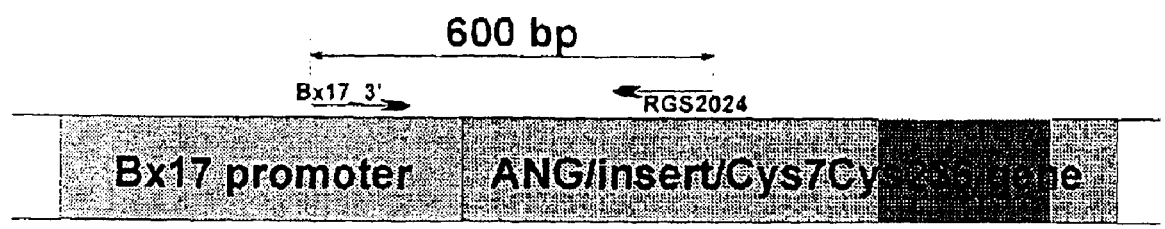

FIG. 15: Schematic of the method of producing a modified seed storage protein containing a binding domain for a macromolecule. In this example, the C-hordein gene is altered to produce an analogue glutenin (ANG) protein containing cysteine residues in the N- and/or C-terminal domains. This protein is then further modified by replacement of part of its repetitive domain with a binding domain from another protein. The addition of cysteine residues allows for the incorporation of the protein into, for example, the gluten macropolymer in wheat flour. The addition of a specific binding domain provides for the non-covalent linkage of the gluten network to other macromolecules (e.g. starch, lipids). Such a protein may be expressed in recombinant bacteria, yeast, or other heterologous host for use as an ingredient or additive, or it may be produced in the seed of a transgenic plant, for example wheat.

FIG. 16: Schematic of the scheme for identifying transgenes in transformed wheat plants by polymerase chain reaction (PCR). A primer pair straddling the interface between the gene and its promoter (from the gene for the high molecular weight glutenin Bx17) ensures that no false positives are detected arising from the high homology between C hordein and gliadin genes.

FIG. 17: Agarose gel showing PCR-based identification of a transgenic wheat plant containing a gene for a modified seed storage protein with incorporated ligand-binding domain. In this example, the gene for ANG/OHBD/Cys7Cys236 was detected in the plasmid used for transforming the wheat plant (lane 1) and in a putative transformant wheat plant (lane 2), but is not detected in a non-transformed control wheat plant (lane 3).

FIG. 18: Starch-binding activity of ANG/SBD/Cys7Cys236 protein assayed by native-PAGE. Protein from each of fraction 6 and 7 from the β-cyclodextrin affinity column of the urea extract of strain AD494(DE3)/pET-SBD was loaded onto native gels containing starch (panels B and D) and/or β-cyclodextrin (panels C and D) or neither starch nor β-cyclodextrin (panel A). The reduction in electrophoretic mobility in the presence of starch alone (panel B) is indicative of the specific starch-binding activity of each protein.

FIG. 19: Demonstration of the oxidative polymerisation of a modified seed-storage protein containing a macromolecule-binding domain. In this example, ANG/SBD/Cys7Cys236 was oxidised to form disulphide-linked polymeric species (indicated by arrows in the scanned image of the SDS-PAGE gel; lanes 1, 2) in the presence or absence of added α-cyclodextrin. The polymeric species were capable of being subsequently reduced by the disulphide-specific reductant dithiothreitol (DTT; lanes 3, 4), showing that the polymerisation was due to the presence of introduced cysteine residues at the N- and C-termini of the ANG portion of the molecule.

M=molecular weight markers with masses indicated (kDa);
Lane 1=ANG/SBD/Cys7Cys236 oxidised in the presence of β-cyclodextrin;
Lane 2=ANG/SBD/Cys7Cys236 oxidised in the absence of β-cyclodextrin;
Lane 3=ANG/SBD/Cys7Cys236 oxidised in the presence of β-cyclodextrin and then reduced with DTT;
Lane 4=ANG/SBD/Cys7Cys236 oxidised in the absence of β-cyclodextrin and then reduced with DTT;
Lane 5=reduced ANG/SBD/Cys7Cys236 in the presence of β-cyclodextrin;
Lane 6=reduced ANG/SBD/Cys7Cys236 in the absence of β-cyclodextrin.

MODES FOR CARRYING OUT THE INVENTION

Materials and Methods

Bacterial Strains and Plasmids

*Escherichia coli* strain DH5α was used as cloning host strain and *E. coli* strain AD494(DE3) (Novagen) was used as the expression host in this work.

pGEM-T (Promega) was used as cloning vector of PCR products. pJKKm(−) (Kirschman and Cramer, 1988) served as cloning vehicle for fusion protein genes. New, assembled genes for expression were sub-cloned into plasmid pET-11d (Novagen).

Cloning of ANGΔCYs7CYs236

Restriction endonucleases and DNA modifying enzymes were from New England Biolabs and Promega Corp. Other chemicals and reagents were of analytical reagent grade. Oligonucleotide primers were synthesised on an Applied Biosystem 394 DNA/RNA Synthesiser using standard phosphoramidite chemistry and were deprotected by heating in ammonium hydroxide solution. Primers were lyophilised and dissolved in TE buffer.

To amplify up a 477 bp long fragment (approximately ⅔ of the whole gene) of C hordein (Accession X60037) from the genomic clone (Lambdahor1-17) of barley by polymerase chain reaction two specially designed primers were used.

terminator cycle sequencing protocol (Perkin-Elmer). One plasmid isolate, containing the ANG gene, was designated as pGEM-ANG.

This plasmid contained two NdeI restriction sites, one within the gene and one within the pGEM-T multiple cloning site (MCS). To make it unique, the ANG gene was subcloned into pJKKm. Because pJKKm has a HindIII site in MCS, it had to be deleted before subcloning.

One ug of the plasmid was digested with 5 units of HindIII enzyme in 20 ill. Mung Bean Nuclease was used to remove the 5' overhang. Two µl of 10X ZnSO$_4$ solution and 0.02 units of enzyme was added to the reaction mix and incubated at 30° C. Reaction mix was extracted once with phenol/chloroform after one hour incubation. DNA was recovered with ethanol precipitation and resuspended in 50 µl. An aliquot of 10 µl of the DNA solution was used for ligation. Ligation was carried out in 15 µl solution at 4° C. overnight using T4 DNA ligase. The ligation mixture was used to transform competent cells of *E. coli* strain DH5α by electroporation. Colonies were grown in LB medium supplemented with kanamycin (50 mg/l). Plasmid was purified from three colonies as mentioned above. DNA samples were tested by performing HindIII enzyme digestions. One clone not containing a HindIII site was chosen and designated as pJKK-H.

pJKK-H was cut with SphI and BanHI to subclone pGEM-ANG SphI-BamHI fragment into the plasmid. Both digested DNA-were purified on QIAquick columns as described earlier, and ligated in 10 µl solution overnight at 14° C. using T4 DNA ligase at a molar ratio of 50:1. Transformed *E. coli* competent cells was spread onto LB medium with kanamycin. Colonies were tested for insert-bearing plasmid DNA by PCR and 3 positive clones were sequenced as above. One clone was designated as pJANGΔCys7Cys236 and used for further cloning work to assemble genes for fusion proteins. Nucleotide and amino acid sequences of this cloning vehicle are shown in FIG. 1.

Design and Cloning of Oleosin Hydrophobic Binding Domain

The sequence of oleosin hydrophobic binding domain (OHBD) was designed to include the consensus sequence of three (maize, rice and barley) oleosin proteins. The sequence

```
oligonucleotide 1 (SEQ ID NO: 1):
     Met Arg                 Cys
5' GTC ATG AGG CAA CTA AAC CCT TGC AGC CAA GAG TTG CAA TC 3'
   BspH I oligonucleotide 2 (SEQ ID NO: 2):
     *** Val              Cys          Gln Gln Pro
5' GGA TCC CTA GAC CAT ACT CCA TAT GCA TGA AGC TTG TTG GGG
   BamH I              Nde I        HindIII

GAC TGG TTG 3'
```

Figure 2:
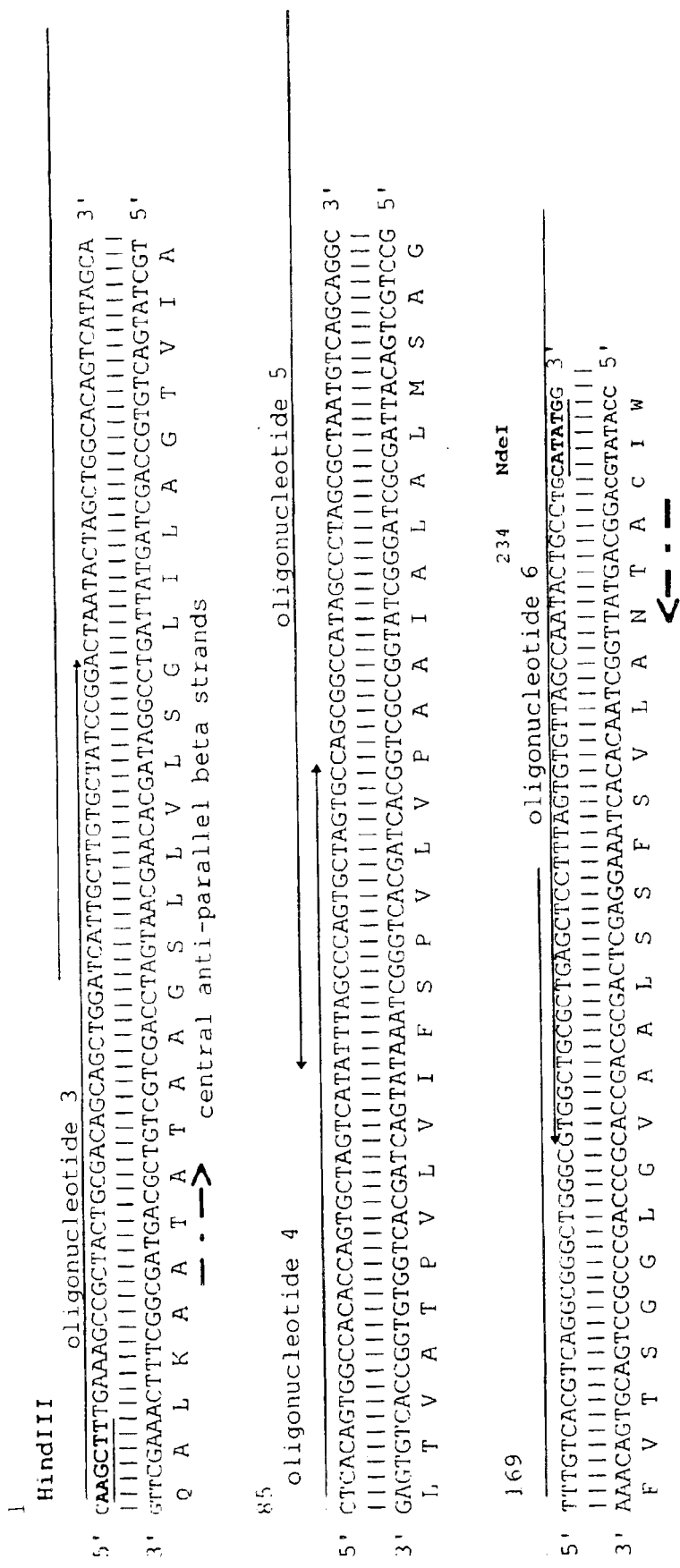
FIG. 2: Nucleotide (SEQ ID NO: 16) and amino acid sequence (SEQ ID NO: 17) of Oleosin Hydrophobic Binding Domain (OHBD). Arrowheads are indicating the direction of primer extension. Smaller letters are indicating extra nucleotides for cloning and amino acids from ANG molecule. Amino acid sequence of the central anti-parallel domain is designated by two arrows.
Figure 7:
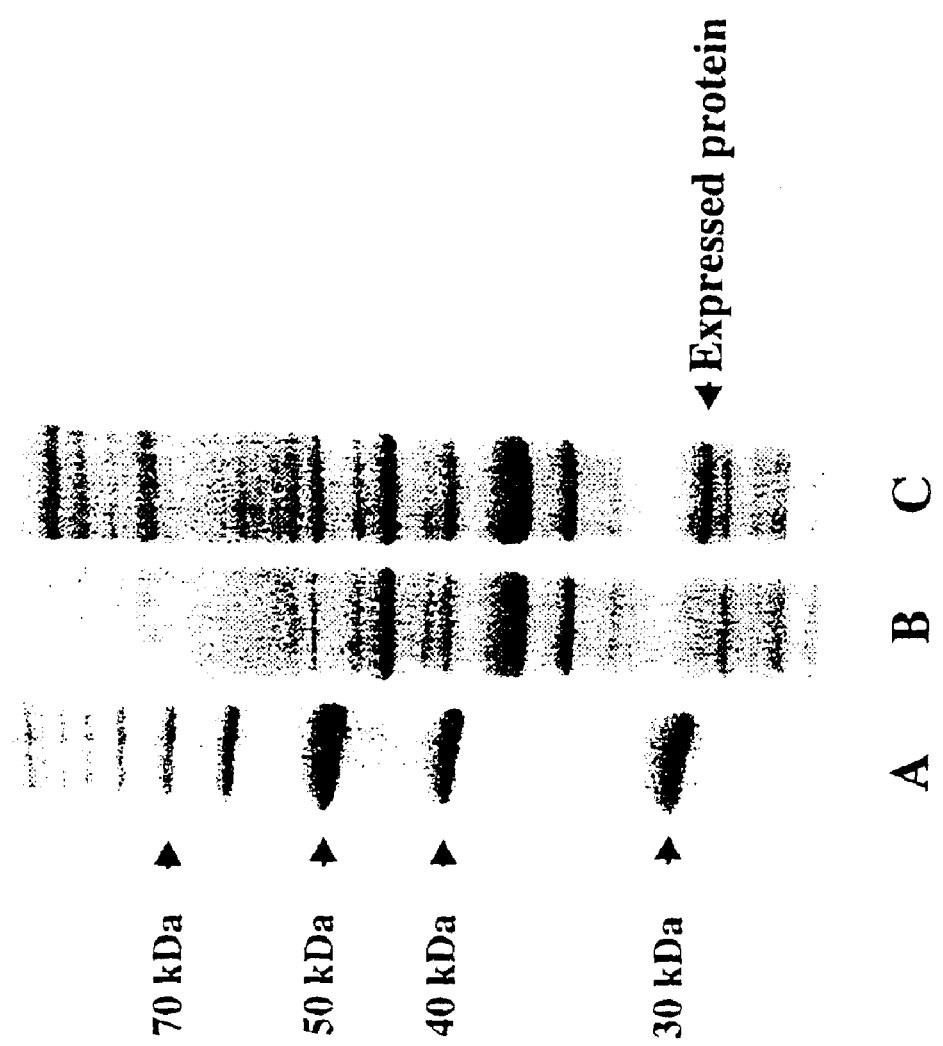
FIG. 7: Expression of the ANG/OHBD/Cys7Cys236 gene. SDS-PAGE analysis followed by Coomassie blue staining. Lane A contains standard molecular weight markers. Lane B shows a control in which the host *E. coli* cell contains the pET-11d vector. Lane C shows the expression of the recombinant ANG/OHBD/Cys7Cys236 protein (migrating slightly further than the 30 kDa marker) from pET-11d containing the ANG/OHBD/Cys7Cys236 gene.
Figure 8:
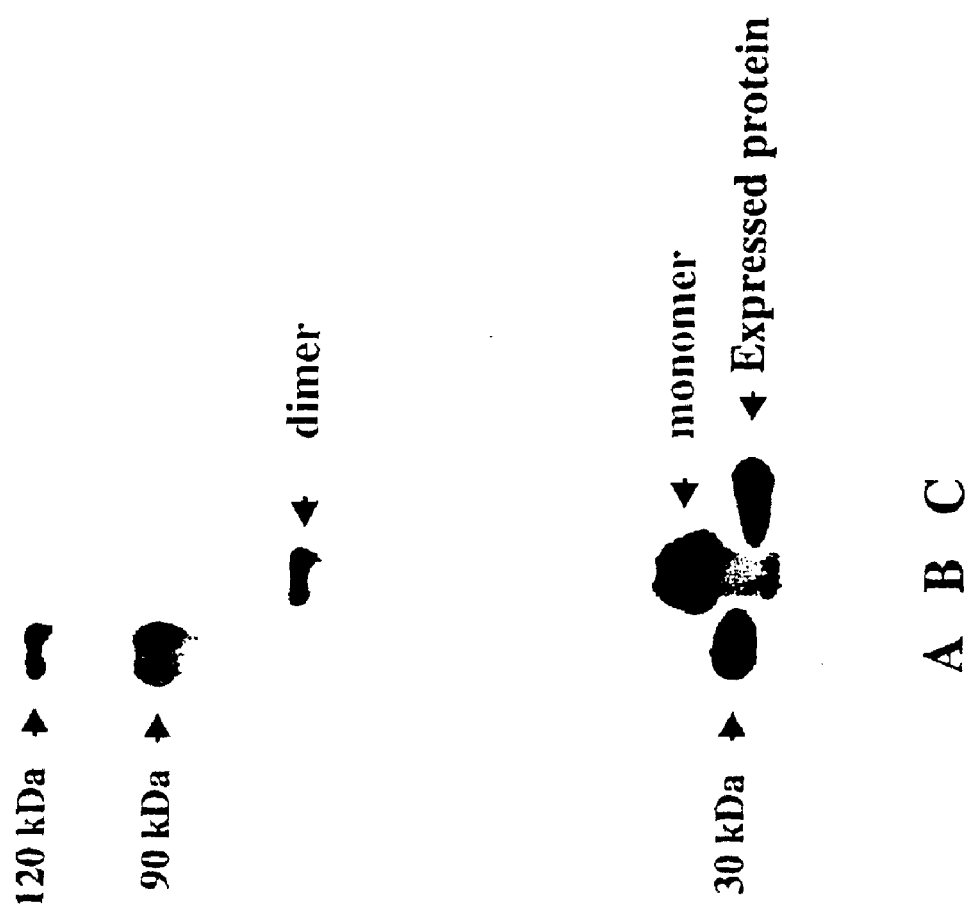
FIG. 8: Expression of the ANG/OHBD/Cys7Cys236 gene. SDS-PAGE analysis followed by Western blot using antibodies to C-hordein. Lane A contained standard molecular mass markers. Lane B contained extract of an *E. coli* cell expressing a modified C-hordein gene containing a single cysteine in the N-terminal region. Lane C contained extract from *E. coli* containing the ANG/OHBD/Cys7Cys236 gene in the pET-11d expression plasmid.

The reaction was performed in an FTS-4000 Thermal Sequencer (Corbett Research, Australia), with 1 cycle of 3 min at 94° C., 20 s at 55° C., 1 min at 72° C.; 36 cycles of 30 s at 94° C., 1 min 30 s at 72° C. The reaction was carried out in 50 ll, containing 45 µl of Supermix (BRL Life Technology) and 1 ng of template DNA and 50 pmol of each oligonucleotides in 5 µl. The DNA was purified following the QIAquick protocol (QIAGEN) and cloned, using the pGEM-T Vector System 1 (Promega) as was recommended by the manufacturer. White transformant colonies selected for growth in LB medium supplemented with ampicillin (100 mg/l) were screened for insert-bearing plasmid DNA by PCR. Plasmid DNA was purified from positive clones using Jetstar miniprep columns (Genomed) and the insert was sequenced in both direction, using the Prism dye is almost identical to the sequence published for barley oleosin isoform-2 (Aalen 1995, Accession Number X82678). Four primers were designed to encode the protein (FIG. 2). The gene was constructed by a modification of the technique of overlap extension, where the two long partially overlapping oligonucleotides were further extended and amplified by shorter external primers, encoding restriction enzyme cleavage sites to clone into pJANGΔCys7Cys236. PCR amplification was performed as above, using the same cycle program and Supermix solution. Concentration of the long oligonucleotides were 0.1 nM, while 2 µM of the short primers in the PCR reaction mix. The PCR product was purified on QIAquick column and cloned into pGEM-T plasmid using Promega kit, as described above. Three positive clones were used for plasmid preparation and sequencing to confirm the nucleotide sequence. One clone was used for further work and called pGEM-OHBD.

Cloning of Starch Binding Domain

The DNA corresponding to the starch binding domain (SBD) of Glucoamylase 1 (1,4-α-D-glucan glucohydrolase) of *Aspergillus niger* (Accession number: X00548) was amplified by PCR from purified genomic DNA. Primers were designed to allow us to add tails at both ends of the DNA fragment for cloning into pJANGΔCys7Cys236 vector.

Sequence of the PCR Primers are:

```
    oligonucleotide 7 (SEQ ID NO: 3):
      Gln Ala Cys Thr
    5' CAA GCT TGT ACC ACT CCC ACC GCC 3'
       Hind III oligonucleotide 8 (SEQ ID NO: 4):
         Ile Cys Arg
    5' CCA TAT GCA CCG CCA GGT GTC AGT CAC 3'
       Nde I
```

Amplification, cloning into pGEM-T and sequencing was done as described above. One clone bearing the gene fragment was designated as pGEM-SBD.

Cloning of CM16 and CM17 Genes for Fusion

Both genes were amplified from purified wheat (*Triticum aestivum*) genomic DNA by PCR.
Nucleotide 9 (SEQ ID NO: 5):
5' GTC GGC AAT GAA GAT TGC ACC 3'
Nucleotide 10 (SEQ ID NO: 6):
5' TCC AAC TGC GTT CTC CTC TTG GCC 3'
Nucleotide 11 (SEQ ID NO: 7):
5' GGA TCC CTA GCT CCA CTG AGA CTC 3'.

For CM16 gene (accession number X55455) oligonucleotide 10 and 11, while for CM17 gene (accession number X59791) 9 and 11 pairs were used. Clones were called pGEM-CM16 and pGEM-CM17, respectively. For subcloning into pJANGΔCys7Cys236 vector, the genes were PCR amplified again, using pGEM clones as template, purified on QIAquick column and digested with the appropriate enzymes. Primers used in this amplification were: nucleotide 12 (SEQ ID NO: 8):

```
           Gln Ala Leu Gly
    5' TGC GCT CAA GCT TTA GGC AAT GAA GAT TGC ACC 3'
              Hind III nucleotide 13 (SEQ ID NO: 9):
              Ile Cys Ser
    5' CAT ACT CCA TAT GCA GCT CCA CTG AGA CTC 3'
              Nde I
```

Cloning Puroindoline a Gene for Fusion

Lambda genomic clone for puroindoline A (PIN-A), kindly provided by Sadequer Rahman, was used as template to amplify the gene (accession number X69913) by PCR. Primers were designed as follows;

```
    oligonucleotide 14 (SEQ ID NO: 10):
      Gln Ala Tyr
    5' CAA GCT TAC GAT GTT GCT GGC GGG 3'
       Hind III oligonucleotide 15 (SEQ ID NO: 11):
    5' CCA TAT GCA CCA GTA ATA GCC AAT AGT GC 3'
       Nde I
```

PCR product was purified, ligated into pGEM-T and sequenced as described above. One clone was used and designated as pGEM-PIN-A.

Fusion of Genes or Gene Fragments with Ang Molecule pJANGΔCys7Cys236 vector was cut with NdeI and HindIII restriction enzymes as all the other pGEM clones and purified on QIAquick columns. Ligation was performed at 14° C. overnight in 10 μl of solution containing T4 DNA ligase and insert:vector at about 20:1 molar ratio. One μl of ligation mix was used for transformation of *E. coli* competent cells and spread onto LB plate with kanamycin. Three fusion gene containing colonies were picked up from each transformation for plasmid preparation and sequencing. The clones were called, for example, pJANG/OHBD/Cys7Cys236 in case of the oleosin binding domain containing ANG molecule.

The fused genes were subcloned into pET-11d expression vector between NcoI and BamHI sites. These clones were called, for example, pET-ANG/OHBD/Cys7Cys236.

Sequence of PCR Primers for Detection of Genes for ANG/domain/Cys7Cys236 in Recombinant Wheat The primers used for the detection of genes for ANG/domain/Cys7Cys236 in recombinant wheat are set out below.

| Primer | Length | Sequence | Designation |
|--------|--------|----------|-------------|
| Bx17_3' | 23 | CAACCATGTCCTGAACCTTCACC | SEQ ID NO:12 |
| RGS2024 | 18 | TGGCTGTTGAGGTTGCAC | SEQ ID NO:13 |

Expression of Fusion Proteins

For protein expression one of the pET clones were transformed into *E. coli* strain AD494(DE3) one day before expression work started.

Small scale expression was carried out in 5 ml 2YT medium, supplemented with ampicillin (100 mg/l) using one transformant colony. After about 5 hours from inoculation (OD600=0.4), expression of the protein was induced by addition of 0.4 mM isopropyl-β-D-thiogalactopyranoside (IPTG). Both induced and uninduced cultures were further incubated for 4 hours at 37° C. Expression was monitored by SDS-PAGE according to Laemmli (1970).

Large scale expression was performed in a shaking flask. One liter 2YT medium was inoculated with 1 ml of overnight culture and induced to express protein by addition of 0.4 mM IPTG at a cell density of ~0.6 Ab. The culture was incubated with shaking overnight and cells were harvested by centrifugation.

Detection of Proteins

PAGE gels were stained overnight with 0.025% Coomassie Blue R-250 in 10% TCA. Excess stain was washed away by water-ethanol-acetic acid (8:1:1) solution.

Immunological detection of the PIN-A containing fusion protein was carried out using the method of Ciaffi et al., (1999). The antibody was raised against puroindoline crude extract, kindly provided by Sadequr Rahman.

Other chimeric proteins were detected in immunoblots using an antibody raised against Hordein, kindly provided by John Skerritt.

Purification of the Fusion Proteins

Expressed ANG/CM16/Cys7Cys236, ANG/CM17/Cys7Cys236 and ANG/SBD/Cys7Cys236 proteins were purified following the method published elsewhere (Tamas et al., 1998), except for the precipitation step. In this work 2 volumes of 1.5 M NaCl were mixed with the 70% ethanol extract, rather than 4 volumes of acetone.

Figure 17:
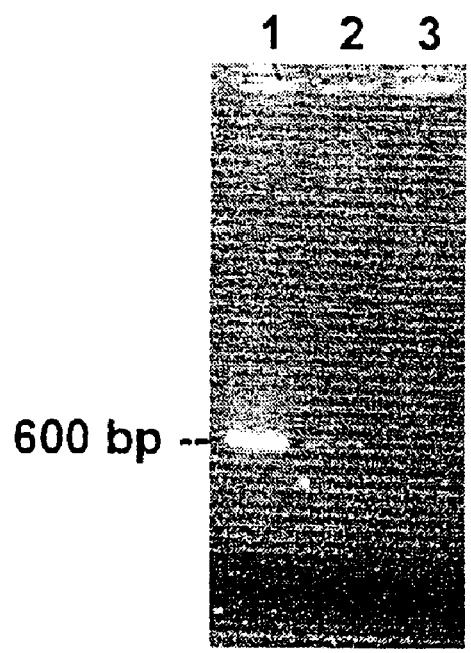

Detection of the Gene Encoding Modified Seed Storage Proteins in Transgenic Wheat Plants The presence of the gene for modified proteins in transgenic wheat plants was determined by polymerase chain reaction (PCR). Reactions were carried out in 11.6 μl volume containing 9 μl PCR Supermix (GibcoBRL), 50 ng template DNA (extracted from wheat leaf tissue using standard protocols), 172 nmol of each of primers Bx17_3' and RGS2024, and 0.6 µl of 25 mM MgCl$_2$. The PCR conditions were 1 cycle of 94° C. for 2 min; 35 cycles of 94° C. for 30 sec, 60° C. for 30 sec, 72° C. for 1 min; 1 cycle of 72° C. for 4 min, 25° C. for 1 min. The results for one plant containing the gene for ANG/OHBD/Cys7Cys236 are shown in FIG. 17. The PCR product of approximately 600 base pairs is indicative of the presence of the gene. A 600 bp PCR product is not obtained in PCR reactions from negative control plants.

RESULTS

Design, Construction and Cloning of pJANGΔCys7Cys236

The gene selected to construct this vector for fusion protein coded for C hordein. This molecule is a storage protein from barley endosperm and characterised by an absence of cysteine residues. The barley genomic clone encodes a molecule of 261 residues, including a 20 residue signal peptide. The gene for mature protein (molecular mass 28 kDa) has 723 nucleotides, including a 669 bp long fragment for a central repetitive domain. The oligonucleotides for PCR were designed to reduce the size of the central part and substitute one residue by cysteine in both unique terminal domains. Oligonucleotide 1 binds to the 5' end of the gene and has an additional sequence at the 5' end to incorporate an initiation ATG codon for methionine and a restriction site for BspHI. Oligonucleotide 1 has a T at position 22 to replace an A to change the codon of serine to cysteine at position 7. The 3' end of oligonucleotide 2 is complimentary to a sequence in the repetitive domain between 430 and 448 nucleotides. This is a rather unique sequence within the strongly repetitive region and also codes for an end of a repeat motif. The amplified gene contains only a 411 bp (137 amino acids) long fragment for central repetitive domain. This oligonucleotide also contains the whole sequence of the C-terminal unique region (6 amino acids) of C hordein and a restriction site for BamHI, immediately after the stop codon. To change the threonine residue at the position of 236 of the full size molecule (six residues from the C-terminal end) the oligonucleotide has a C at position 26 and an A at position 27 to substitute a G and a T, respectively. There is another base pair change in this primer at position 22 to replace C with A, which is a "wobble" base of the isoleucine codon. This substitution allowed the creation of restriction site for NdeI enzyme. Oligonucleotide 2 has also got six nucleotides which are not part of the C hordein gene, coding for alanine and serine. These extra nucleotides were added to create one unique restriction site, close to NdeI, within the ANG gene. The two restriction sites are separated with 4 bp to give easy cleavage for both enzymes. The insertion of a gene for another molecule or fragment of a molecule between HindIII and NdeI enabled the present inventors to create fusion proteins with new, designed characteristics.

The gene for ANGΔCys7Cys236 molecule is 474 bp long and codes for a protein with a molecular mass of 18.5 kDa (FIG. 3).

PCR amplified DNA was cloned, with two steps, into a plasmid, called pJKKm with a modified MCS. Having deleted HindIII restriction site from the original plasmid, the cloning vehicle pJANGΔCys7Cys236 has unique HindIII and NdeI cleavage sites within ANG gene for gene insertion. Size of the vector is 3873 bp and provides kanamycin resistance to host *E. coli* cells. The gene is sitting in the vector with 5' ends close to the SP6 RNA Polymerase transcription initiation site.

Subcloning engineered genes into pET-11d did not require agarose gel purification of the fragments, because of the difference in resistance genes within plasmids.

Expression of ANGΔCys7Cys236 Protein

To check and compare characteristics of this short molecule to hordeinCys7Cys236, it has been expressed in both small and large quantities. Comparison of the SDS-PAGE patterns of the total cell proteins before and 3 hours after induction with IPTG showed a new band in the induced sample. ANG molecule was readily extracted from lysed cells with 70% (v/v) ethanol and precipitated by the addition of 2 volume of 1.5 M NaCl solution. The resulting preparation, in the presence of reducing agent (0.1 M DTT), had the same mobility as the extra band in *E. coli* lysate. Apparent molecular mass of the protein was about 21 kDa, having a slightly lower mobility in the gel. This characteristic is not unusual for storage proteins, In the absence of DTT, the ethanol extracted sample gave a ladder of bands indicating that the protein is able to form long chains through disulfide bonds.

The ability of the ANG molecule to incorporate into the gluten matrix of the dough was confirmed by a series of mixing experiments carried out using small scale testers.

Results of SDS-PAGE and mixing experiments showed clearly that ANGΔCys7Cys236 protein had the same or similar properties as the 2 cysteine residue containing C hordein protein.

Design, Construction and Cloning of Synthetic Gene for Oleosin Hydrophobic Binding Domain (OHBD)

Amino acid sequence was designed according to a comparison of four molecules (one maize, two barleys and one rice), using Genetic Computer Group (GCG) program, called "pileup". OHBD gene fragment, for this work, contain the entire region of the lipophilic stretch of oleosin (FIG. 2), very similar to barley gene (accession number: X82677). Codon usage was designed to avoid long stretch of Gs and Cs, which could have led to mis-annealing and sequencing problems. The 5' flanking region of the gene fragment consisted of a tripeptide sequence, of the amphipathic N terminus, while the 3' end another tripeptide of the C terminus of oleosin. The central anti-parallel beta stranded domain had 71 residues. The turn of the anti-parallel consists of 13 residues and is the most conserved region. The two anti-parallel strands are highly symmetrical in the pairing of residues of similar hydrophobicity on the opposite strands. These characteristics are very similar to those reported for maize oleosin protein (Huang 1996).

The synthetic gene fragment, flanked with two appropriate restriction sites for subcloning, was cloned into pGEM-T vector. One clone, containing the correct sequence of a fragment of 243 bp nucleotides, was designated as pGEM-OHBD. Size of OHBD fragment was 77 amino acids and had a molecular mass of 7 kDa.

Cloning of Starch Binding Domain (SBD)

Glucoamylase 1 from *Aspergillus niger* comprises two domains, one being a catalytic domain (1–470 residues) and the other (509–616 residues) being responsible for binding granular starch (Le Gal-Coeffet et al., 1995).

DNA corresponding to the SBD was amplified by PCR method from *Aspergillus niger* purified genomic DNA, cloned into pGEM-T vector, sequenced and designated as pGEM-SBD. This clone had a 337 bp long fragment (FIG. 4) with two restriction sites for insertion into pJANGΔCys7Cys236 vector and an extra alanine before the very first cysteine of SBD. This residue derived from HindIII restriction site. The binding domain had 108 amino acids, including two cysteines, with a molecular mass of 11.9 kDa.

Cloning of CM16 and CM17 Gene for Fusion

Both CM16 and CM17 (CM refers to Chloroform/Methanol soluble) proteins, reported as members of the α-amylase/trypsin inhibitor family and also reported that specific lipids are tightly bound to the fraction, were purified from wheat (Kobrehel and Sauvaire, 1990). These two molecules are very similar on the amino acid level, but there are a few differences in the distribution of charged residues (FIG. 5).

To clone these two genes, three primers were used to amplify them in two, separate PCR reactions from wheat genomic DNA. One primer (oligonucleotide 11) hybridised to the 3' end of the genes, while to distinguish between the two genes, two specific primers were designed for the 5' ends, pGEM-CM17 clone carried the gene for only the mature protein. However, pGEM-CM16 clone had a few extra base pairs from the signal peptide region. Both clones had a DNA fragment encoding mature chloroform/methanol soluble proteins with 10 cysteine residues and a molecular mass of 13.4 kDa.

To subclone these genes into ANGΔCys7Cys236 carrying vector, two restriction sites were added to one of each ends by PCR, using the same primer pairs for both pGEM clones, as templates. Primer corresponding to the N-terminus of the mature proteins contained nucleotides for HindIII restriction enzyme. It also had an extra alanine residue, and a mutation in the first codon (TTA for leucine), substituting valine (GTC) in CM17 and isoleucine (ATC) in CM16 molecule, because of the sequence requirement for HindIII enzyme. The fragment cloned into ANG cloning vehicle had 360 nucleotides.

Cloning Puroindoline A (PIN-A) Gene for Fusion

The clone for PIN-A protein, which is capable of binding tightly to both wheat phospholipids and glycolipids (Dubreil et al., 1997), was kindly provided by S. Rahman, derived from a genomic library.

PCR amplified DNA encoded for a 121 amino acid long fragment of puroindoline A, 5 residues shorter in the N terminal region than the mature protein. This shorter protein had 10 cysteine residues and a molecular mass of 14.3 kDa (FIG. 6), For insertion into ANG molecule, the pGEM-PIN-A clone also carried two restriction sites (HindIII and NdeI) and an extra alanine, because of HindIII site requirement.

Expression of ANG/OHBD/Cys7Cys236 Protein

Having inserted OHBD gene fragment into pJANGΔCys7Cys236 cloning vehicle, the entire gene was subcloned into expression vector pET-11d. Protein was expressed in *E. coli*, using AD494(DE3) strain. This genetically engineered new gene (717 bp long) coded for a protein with a molecular mass of 25.5 kDa.

Cells were harvested by centrifugation after overnight expression (5 ml culture) and resuspended in 100 μl gel loading buffer (0.125 M TRIS/HCl pH 6.8, 4% SDS, 10% (v/v) glycerol), containing 0.1 M DTT. Proteins were analysed by SDS-PAGE and stained with Coomassie blue (FIG. 7). Lane A contains standard molecular weight markers, lane B shows a control in which the host *E. coli* cell contains the pET-11d vector, and lane C shows the expression of the recombinant ANG/OHBD/Cys7Cys236 protein (migrating slightly further than the 30 kDa marker) from pET-11d containing the ANG/OHBD/Cys7Cys236 gene. The apparent molecular mass of the newly synthesised protein (~29 kDa) was larger than that calculated on the basis of the nucleotide sequence of DNA. A similar characteristic has been observed previously for different prolamines of cereals. This fusion protein consisted of part of a prolamine and a part of an oleosin molecule. C hordein had been considered as a rod shaped molecule, while oleosin hydrophobic binding domain has anti-parallel strands, which would penetrate into the oil body and thus anchor the protein stably. It means that none of the two fragments has globular structure as compared with the molecular weight marker molecules. Discrepancy in apparent molecular mass on SDS-PAGE was lower mobility. FIG. 8 shows a Western blot of an SDS-PAGE gel (run in the absence of reducing agents such as dithiothreitol) using antibodies to the C-hordein protein. Lane A contained standard molecular weight markers, lane B contained extract of an *E. coli* cell expressing a modified C-hordein gene containing a single cysteine in the N-terminal region, and lane C contained extract from *E. coli* containing the ANG/OHBD/Cys7Cys236 gene in the pET-11d expression plasmid. The strong antibody cross reaction to hordein antibodies at 29 kDa confirms that the 29 kDa protein is the product of the ANG/OHBD/Cys7Cys236 gene.

Expression and Analysis of ANG/PIN-A/Cys7Cys236 Protein

A DNA fragment comprised of ANGΔCys7Cys236, and Puroindoline-A genes with a length of 840 nucleotides from kanamycin resistant plasmid (see above) was subcloned into pET-11d expression vector. One transformant colony was picked up and transferred into 5 ml of 2YT medium. Protein expression was induced by IPTG and after 2 and 6 hours cells were harvested by centrifugation and resuspended in 200 μl of gel loading buffer. SDS-PAGE analysis of protein content of bacteria, before and after induction, is shown on FIG. 10. Lane A contained standard protein molecular mass markers. Lane B contained extract of cells harbouring the control pET-11d plasmid, lanes C and D contained extracts of cells harbouring the pET-11d vector containing the ANG/PIN-A/Cys7Cys236 gene. Lane C contained extract 2 hours after IPTG induction, lane D contained extract prepared 6 hours following IPTG induction. An extra protein band appeared on gel with an apparent molecular mass of 35 kDa, after induction (lane D). This expressed protein positively reacted with puroindoline A antibody (FIG. 11). Lanes A and B contained extract of cells harbouring pET-11d containing the ANG/PIN-A/Cys7Cys236 gene, 2 hours and 6 hours after induction respectively. Lane C contained a Western blot of cells harbouring a plasmid containing the puroindoline A gene alone (not inserted into the ANGΔCys7Cys236 gene), and lane D contained extract of cells harbouring the control pET-11d vector. All lanes were reacted with anti-puroindoline A antibody. FIG. 12 shows a Western blot of an SDS-PAGE gel reacted with anti-hordein antibodies. Lane A contained molecular mass markers, lane B contained extract of cells harbouring the control pET-11d vector, lane C contained extract of cells harbouring a plasmid which contains the puroindoline A gene alone, and lane D contained extract of cells harbouring pET-11d vector containing the ANG/PIN-A/Cys7Cys236 gene. The expressed protein is clearly seen in lane D.

Analogue glutenin-puroindoline A fusion protein had a slightly lower mobility on SDS-PAGE as it was calculated (32.8 kDa) on the basis of amino acid sequence. This small difference was probably due to the rod shape of the ANG part of the molecule. Expressed puroindoline A protein, however, had the same mobility as it was calculated.

Expression of Modified Proteins Following Wheat Transformation

Microprojectile bombardment is currently the most widely applied technique used to transfer genes into wheat. The transfer of genes into wheat and their expression is carried out using specific DNA constructs containing a selectable marker gene and the gene-of-interest respectively. The selectable marker gene used was contained on the plasmid pEmuKON (Chamberlain et al., 1994). Constructs for the gene-of-interest constructs are shown in FIG. 13. Wheat transformation was carried out using paromomycin selection according to the procedures outlined in Witrzens et al., 1998).

Expression, Purification and Analysis of ANG/SBD/Cys7Cys236 Protein

PET11d and the derivative of that plasmid containing the gene for ANG/SBD/Cys7Cys236 protein (pET-SBD) were separately transformed into strain AD494(DE3). One transformant colony of each was used to inoculate 5 ml cultures of LB media containing 200 mg/i ampicillin. After 4 hours shaking at 37° C. these cultures were used to inoculate 600 ml of the same media in 2 l flasks, and these were incubated with shaking overnight (16 hours) at 37° C. IPTG was added to these cultures 6 hours after inoculation to induce expression of protein from the plasmids. Cells from each culture were harvested by centrifugation at 10,000 g for 15 min at 5° C.

One half of the cells from each culture were lysed by incubation for 30 min at room temperature in 35 ml of 50 mM Tris-Cl buffer pH 7.5 containing 8 M urea, 5 mM EDTA and 1 mM DTT. Insoluble material was removed by centrifugation at $2 \times 10^5$ g for 1 hr at 15° C. The supernatants were then extensively dialysed against the extraction buffer minus urea (50 mM Tris-Cl pH 7.5, 5 mM EDTA, 1 mM DTT) at 5° C. The cloudy precipitates were removed by centrifugation at $2 \times 10^5$ g for 1 hr at 5° C. and the supernatants (35 mL) stored at −20C.

β-Cyclodextrin-binding proteins were purified from 20 ml of each of the two dialysed and clarified bacterial extracts by passage through a 5 ml cyclodextrin-sepharose column equilibrated with 50 mM Tris-Cl pH 7.5, 100 mM NaCl, 40 mM dithiothreitol, 1 mM EDTA (column buffer). After loading, the column was washed with 20 ml column buffer and bound proteins eluted with 25 ml column buffer containing 15 mM β-cyclodextrin. Five ml fractions were collected during loading, washing and elution of the column. Fractions were dialysed extensively against water, lyophilised and resuspended in 0.1 M Tris-Ci pH 6.8 at ca. 1 $\mu$l 0 per ml equivalent of the original bacterial cell culture.

Figure 14:
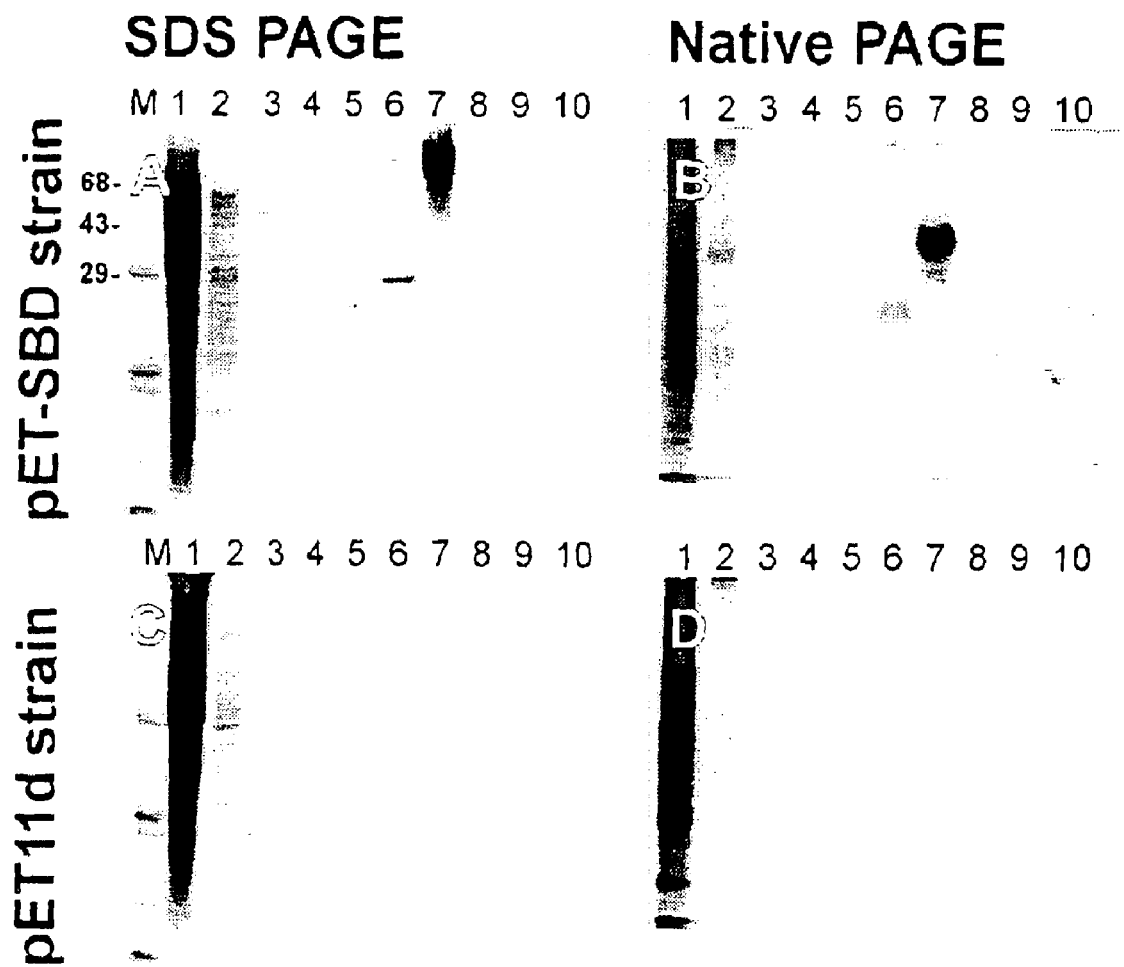
FIG. 14: Expression and β-cyclodextrin affinity purification of ANG/SBD/Cys7Cys236. Native- and SDS-PAGE gels of column fractions from a 5 ml β-cyclodextrin-sepharose affinity column loaded with extracts from IPTG-induced cultures of strain AD494(DE3) bearing either pET11d control plasmid or the pET-SBD plasmid for the expression of ANG/SBD/Cys7Cys236.

Native- and SDS-PAGE gels of the final load fraction and the wash and elution fractions are shown in FIG. 14. Each lane contained protein from the equivalent of 7 ml of the bacterial culture. Two major β-cyclodextrin-binding proteins were seen in the elution fractions (see lanes 6 and 7) from the strain bearing plasmid pET-SBD. These are estimated to be 30 kDa and >60 kDa from the SDS-PAGE gel. A 30 kDa protein was also eluted from the column of the extract from the control strain bearing plasmid pET11d (panel C, lane 6), but it is not produced to the same level as in the former strain.

Expression, Purification and Analysis of ANG/CM16/Cys7Cys236 Protein

The gene for this fusion protein (834 bp long) was subcloned, from kanamycin resistant, pJKKm originated plasmid, into the ampicillin resistant pET-11d expression vector, as above. Bacteria was grown at 37° C. until OD600 reached 0.6 units, then expression was induced by adding IPTG. Cells were harvested two, four or six hours after induction and samples were prepared as in case of SBD chimeric protein.

Figure 9:
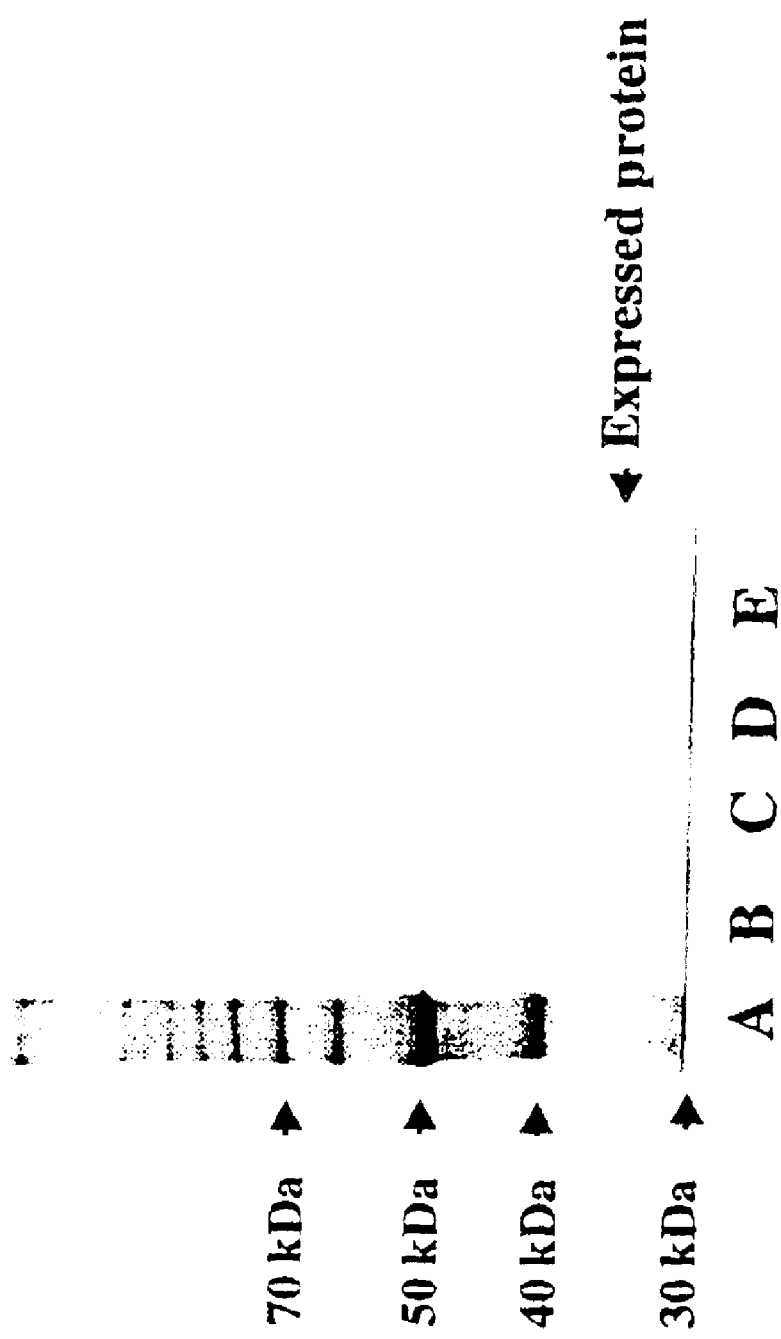
FIG. 9: SDS-PAGE analysis of the purified ANG/CM16/Cys7Cys236 gene product by Coomassie blue staining. Lane A contains standard protein molecular weight markers. Lanes B to E show ethanol-soluble extracts of the crude *E. coli* lysates. Lane B contained extract from cells containing the control plasmid, pET-11d. Lanes C, D and E contained ethanol soluble extracts of cells harbouring the pET-11d vector containing the ANG/CM16/Cys7Cys236 gene, prepared from cells 2, 4 and 6 hours, respectively, after induction of protein synthesis using IPTG.
Figure 10:
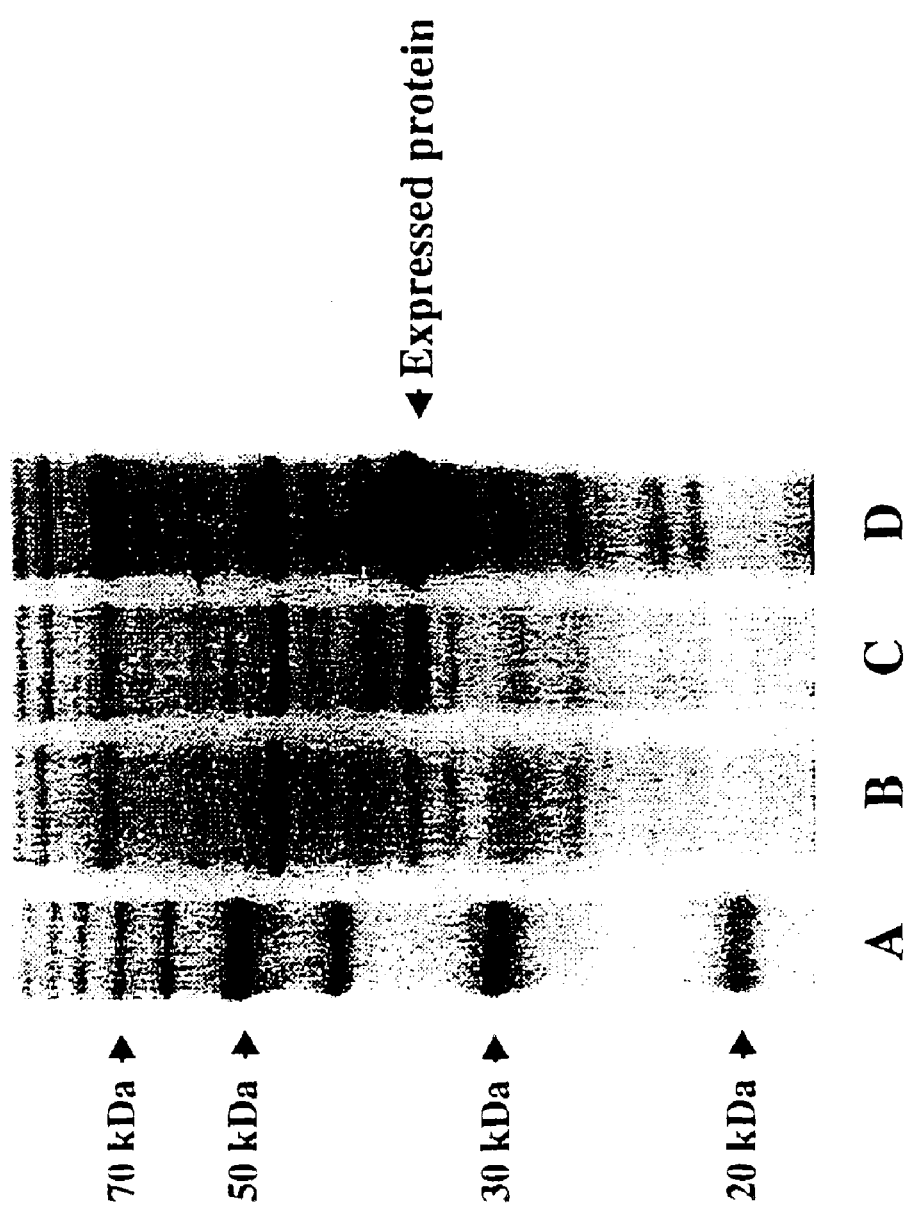
FIG. 10: Expression of the ANG/PIN-A/Cys7Cys236 gene. SDS-PAGE gel stained with Coomassie blue. Lane A contains standard protein molecular weight markers. Lane B contained extract of cells harbouring the control pET-11d plasmid, lanes C and D contained extracts of cells harbouring the pET-11d vector containing the A-NG/PIN-A/Cys7Cys236 gene. Lane C contains extract 2 hours after IPTG induction, lane D contains extract prepared 6 hours following IPTG induction.
Figure 11:
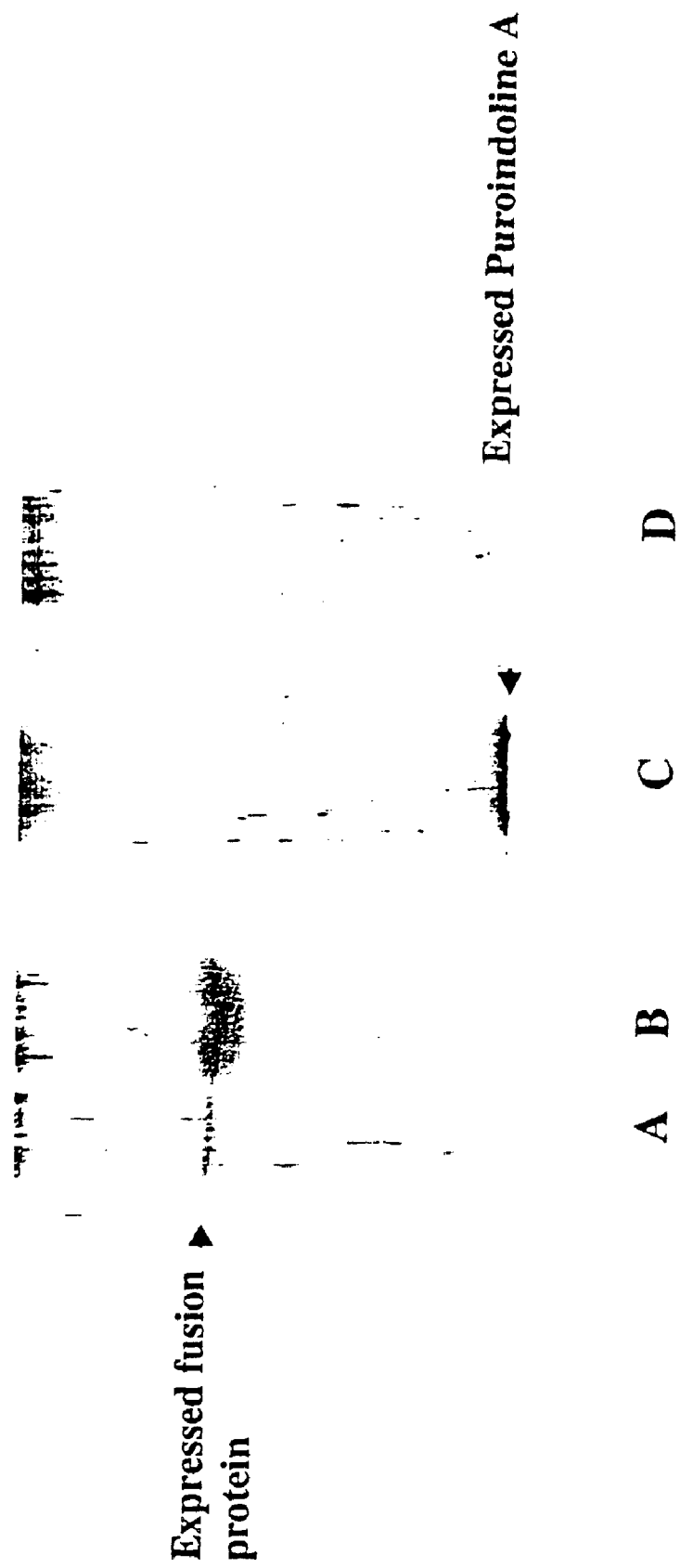
FIG. 11: Expression of the ANG/PIN-A/Cys7Cys236 gene. SDS-PAGE analysis followed by Western blotting with anti-puroindoline A antibodies. Lanes A and B contained extract of cells harbouring pET-11d containing the ANG/PIN-A/Cys7Cys236 gene, 2 hours and 6 hours after induction respectively. Lane C contains a Western blot of cells harbouring a plasmid containing the puroindoline A gene alone (not inserted into the ANGΔCys7Cys236 gene). Lane D contained extract of cells harbouring the control pET-11d vector.
Figure 12:
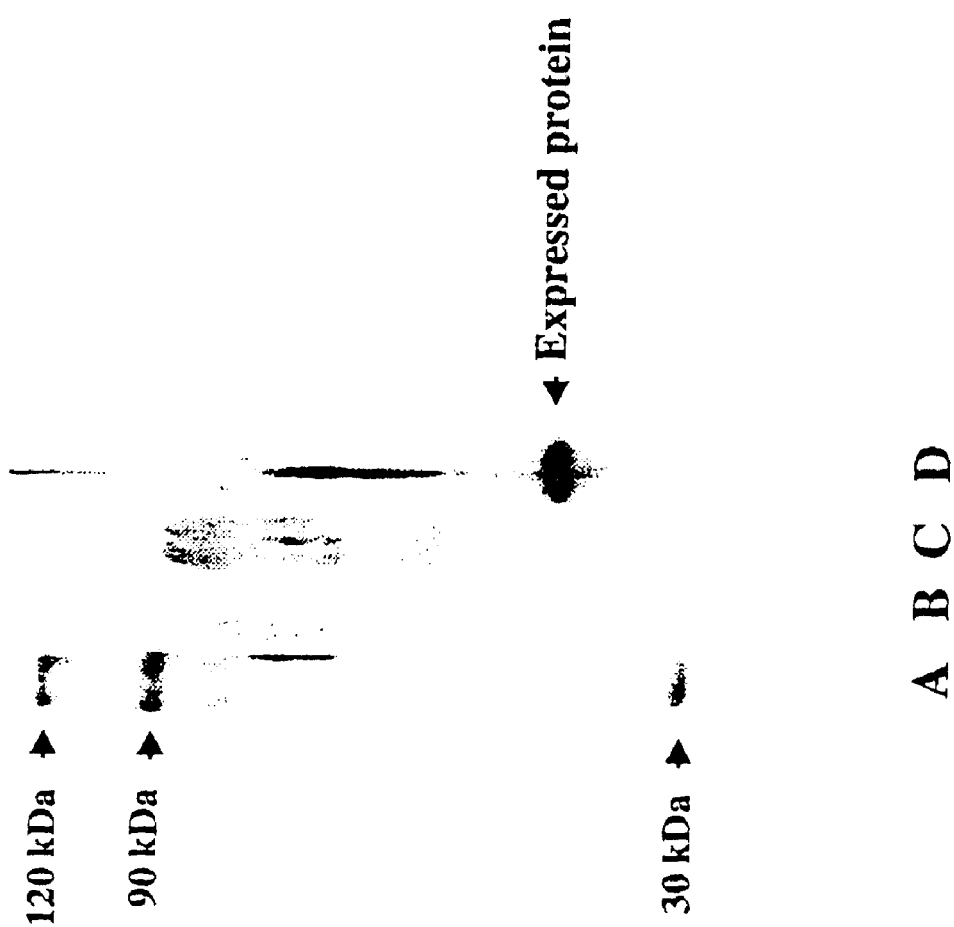
FIG. 12: Expression of the ANG/PIN-A/Cys7Cys236 gene. SDS-PAGE analysis followed by Western blotting with anti-hordein antibodies. Lane A contains molecular weight markers. Lane B contained extract of cells harbouring the control pET-11d vector. Lane C contained extract of cells harbouring a plasmid which contains the puroindoline A gene alone. Lane D contained extract of cells harbouring pET-11d vector containing the ANG/PIN-A/Cys7Cys236 gene.
Figure 13:
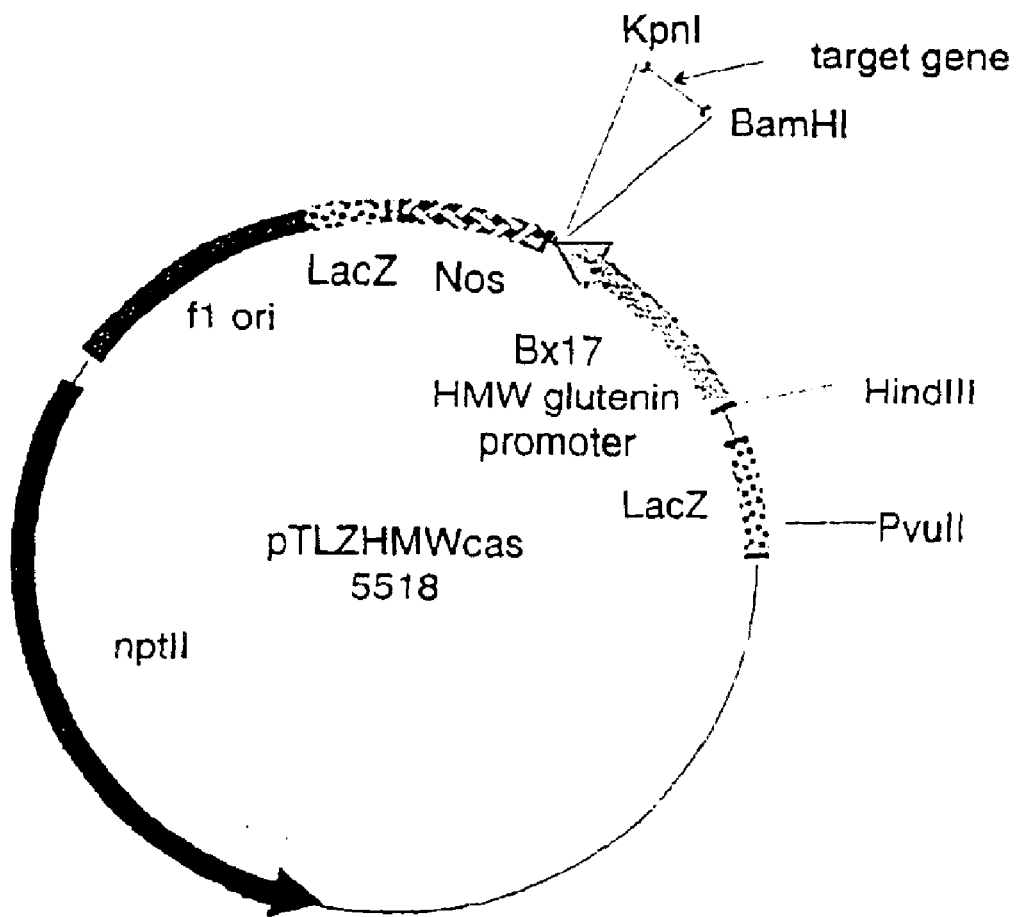
FIG. 13: Plasmids for the transformation of wheat with constructs containing novel protein genes. The vectors are based on the plasmid pTLZHMWcas which has been modified by insertion of genes into the KpnI and BanH1 site region. The vectors are: pTLZ-ANGCys7Cys13, pTLZ-ANGCys236 and pTLZ_ANG/OHBD/Cys7Cys236.

Result of the SDS-PAGE analysis is shown in FIG. 9 (the gel is stained with Coomassie protein stain). Lane A contains standard protein molecular weight markers. Lanes B to E show ethanol-soluble extracts of the crude *E. coli* lysates. Lane B contained extract from cells containing the control plasmid, pET-11d. Lanes C, D and E contained ethanol soluble extracts of cells harbouring the pET-11d vector containing the ANG/CM16/Cys7Cys236 gene, prepared from cells 2, 4 and 6 hours respectively after induction of protein synthesis using IPTG. The ethanol-soluble fraction gave only one band on Coomassie stained gel representing a protein with an apparent molecular mass of 35 kDa. This was also higher than the calculated (31.9 kDa), and this discrepancy is also explained by the unusual shape of the protein.

Yield of protein expression in large scale, in shaking flask was 30 mg protein from 1 liter of medium.

Demonstration of Starch Binding Activity

Figure 18:
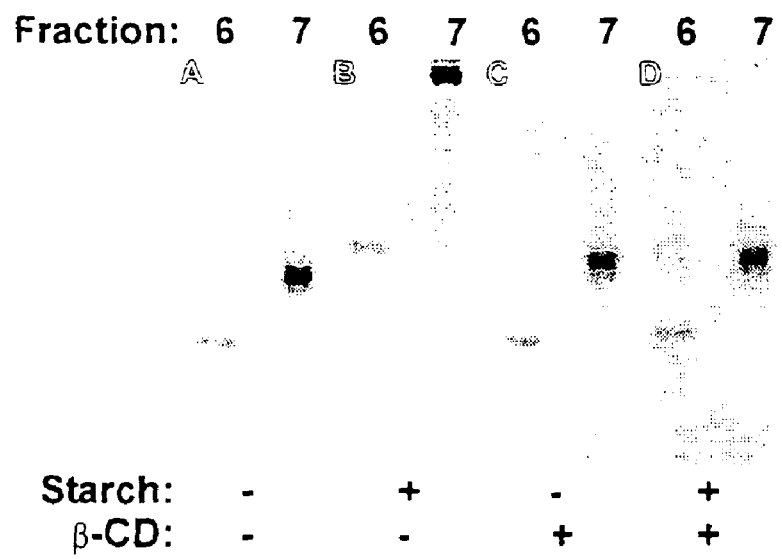

The starch-binding activities of the major proteins in fractions 6 and 7 of the affinity purification column were demonstrated as follows. Fractions were loaded onto four native-PAGE gels containing glycerol (10%6 w/v), CHAPS (0.05% w/v) and various combinations of β-cyclodextrin (5 MM) and starch (corn amylopectin, 0.1% w/v), as indicated in FIG. 18. The mobility of the protein bands in each gel was compared. It was found that the electrophoretic mobility of the major protein band in each fraction was significantly retarded in the presence of starch (FIG. 18, panel B). The specificity of the starch binding activity of these protein bands was demonstrated by its competitive inhibition by β-cyclodextrin (panels C, D).

Identification of the Purified Starch-Binding Proteins by Tryptic-Peptide Mass Fingerprinting and N-Terminal Protein Sequencing The two major protein bands from the native gel of β-cyclodextrin affinity column fractions from strain AD494 (DE3)/pET-SBD were subjected to in-gel tryptic digestion followed by matrix-assisted laser-desorption time-of-flight (MALDI-TOF) mass spectroscopy. The masses of the identified tryptic fragments were compared to the theoretical masses of tryptic peptides expected from ANG/SBD/Cys7Cys236, as well as being used to search the protein sequence databases for other candidate proteins giving matching tryptic peptides.

The 30 kDa protein of fraction 6 (FIG. 14, panels A, B, lane 6) was identified as the periplasmic maltose-binding protein of *E. coli* (product of the malE gene), based on 17 peptide matches covering 57% of the protein sequence.

The major protein band of fraction 7 (FIG. 14, panels A, B, lane 7) was identified as ANG/SBD/Cys7Cys236 on the basis of 4 matching peptides covering 23.11% of the sequence (Table 1). Further proof of the identity of this protein was obtained from N-terminal protein sequencing. Ten cycles of sequencing yielded the sequence:

MRQLNPCSQE which is as expected for ANG/SBD/Cys7Cys236. This provides convincing proof of the identity of the purified protein, and confirms that the functional data are properties of the modified seed storage protein, as designed.

TABLE 1

Mass spectral characterisation of ANG/SBD/Cys7Cys236

| Peptide mass | Expected mass | Start | End | Sequence |
|---|---|---|---|---|
| 1776.74 | 1777.28 | 224 | 238 | IESDDSVEWESDPNR |
| 2193.00 | 2193.85 | 221 | 238 | FIRIESDDSVEWESDPNR |
| 2652.26 | 2653.54 | 198 | 220 | YTSSDPLWYVTVTLPAGESFEYK |
| 2257.03 | 2258.00 | 239 | 258 | EYTVPQAC*GTSTATVTDTWR |

C* = acrylamide adduct of cysteine

Figure 19:
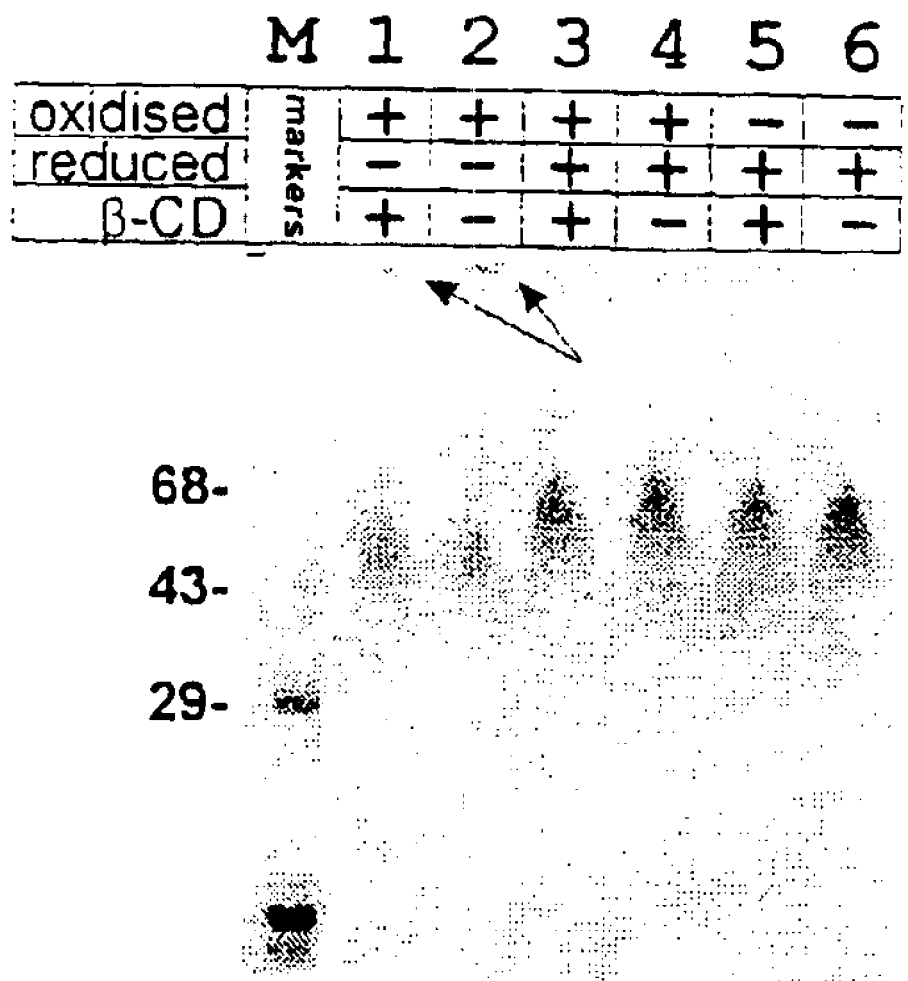

Demonstration of the Ability of ANG/SBD/Cys7Cys236 to form Disulphide-Bonded Polymers The design of the analogue glutenin protein (ANG) included cysteine residues at both N- and C- termini to allow disulphide-mediated incorporation of the modified seed-storage protein into the gluten macropolymer. The present inventors have shown by in vitro polymerisation experiments that the ability of the ANG/domain/Cys7Cys236 proteins to incorporate into disulphide-bonded polymeric species is not impaired by the presence of the extra domain.

The ability to form polymers was demonstrated by copper-mediated oxidation of ANG/SBD/Cys7Cys236 protein int 50 μM Tris-Cl buffer pH 6.8. Three pairs of protein samples were employed, with one of each pair containing add ed s-cyclodextrin (0.5 m to analyse any effect of a ligand on the disulphide-bonding of the ANG. Two pairs were oxidised for 5 min at room temperature in the presence of 0.1 mM $CuSO_4$, before chelation of the metal by addition of EDTA (10 mM). One of these pairs was then reduced in the presence of 20 mM DTT. A further pair of samples had no copper added, but were reduced with DTT in the presence of EDTA. The samples were analysed by SDS-PAGE (FIG. 19). There was no effect on oxidation due to the presence of the ligand β-cyclodextrin. The majority of the oxidised protein sample forms a high molecular weight band which just enters the separating gel (lanes 1, 2). That this change in mobility is due to the formation of disulphide-bond polymeric forms is shown by the ability of the disulphide-specific reductant DTT (lanes 3, 4) to break the polymer back down into the higher-mobility form seen in the reduced sample (lanes 5, 6).

Detection of the Gene Encoding Modified Seed Storage Proteins in Transgenic Wheat Plants.

The presence of the gene for modified proteins in transgenic wheat plants was determined by polymerase chain reaction (PCR). Reactions were carried out in 11.6 μl volume containing 9 μl PCR Supermix (GibcoBRL), 50 ng template DNA (extracted from wheat leaf tissue using standard protocols), 172 nmol of each of primers Bx17_3' and RGS2024, and 0.6 μl of 25 mM $MgCl_2$. The PCR conditions were 1 cycle of 94° C. for 2 min; 35 cycles of 94° C. for 30 sec, 60° C. for 30 sec, 72° C. for 1 min; 1 cycle of 72° C. for 4 min, 25° C. for 1 min. The results for one plant containing the gene for ANG/OHBD/Cys7Cys236 are shown in FIG. 17. The PCR product of approximately 600 base pairs is indicative of the presence of the gene. A 600 bp PCR product is not obtained in PCR reactions from negative control plants.

Demonstration of the Ability of ANG/SBD/Cys7Cys236 to Form Disulphide-Bonded Polymers The design of the analogue glutenin protein (ANG) included cysteine residues at both N- and C-termini to allow disulphide-mediated incorporation of the modified seed-storage protein into the gluten macropolymer. The present inventors have shown by in vitro polymerisation experiments that the ability of the ANG/domain/Cys7Cys236 proteins to incorporate into disulphide-bonded polymeric species is not impaired by the presence of the extra domain.

The ability to form polymers was demonstrated by copper-mediated oxidation of the protein in 50 mM Tris-Cl buffer pH 6.8. Three pairs of protein samples were employed, with one of each pair containing added β-cyclodextrin (0.5 mM) to analyse any effect of ligand-binding on the disulphide-bonding of the ANG moiety. Two pairs were oxidised for 5 min at room temperature in the presence of 0.1 mM $CuSO_4$, before chelation of the metal by addition of EDTA (10 mM). One of these pairs was then reduced in the presence of 20 mM DTT. A further pair of samples had no copper added, but were reduced with DTT in the presence of EDTA. The samples were analysed by SDS-PAGE (FIG. 19). There was no effect on oxidation due to the presence of the ligand β-cyclodextrin. The majority of the oxidised protein sample forms a high molecular weight band which just enters the separating gel (lanes 1, 2). That this change in mobility is due to the formation of disulphide-bond polymeric forms is shown by the ability of the disulphide-specific reductant DTT (lanes 3, 4) to break the polymer back down into the higher-mobility form seen in the reduced samples (lanes 5, 6).

SUMMARY

The demonstration of the binding activity of a modified glutenin according to the present invention was provided in the example given above for what has been termed the ANG/SBD/Cys7Cys236 protein. The data provided supports the demonstration of the expression and purification of a novel protein (apparent molecular mass 60 kDa) from the E. coli strain bearing the expression plasmid (pET-SBD), in comparison to the lack of this protein in the same strain bearing the control plasmid (pET11d) (FIG. 14). The purification involved the use of an affinity chromatography step in which the protein was purified on the basis of its ability to bind to a column matrix containing β-cyclodextrin. The protein was specifically eluted from this column using unbound β-cyclodextrin. This, therefore, represents the first example of how the present inventors demonstrate reduction to practice through the generation of a seed storage protein containing a functional ligand binding domain.

The demonstration of the binding of the major purified proteins to corn starch using native polyacrylamide gel electrophoresis, and the inhibition of this binding by α-cyclodextrin (PAGE) (FIG. 18) is a highly convincing demonstration of reduction to practice of the present invention.

The identification of this protein as ANG/SBD/Cys7Cys236 by peptide mass fingerprinting and N-terminal protein sequencing further demonstrates the functionality of modified seed-storage proteins containing a macromolecular binding domain. The anomolous apparent molecular weight of this protein in SDS-PAGE may be yet another example of the general phenomenon of modified C hordein proteins migrating with unexpected electrophoretic mobility, as the calculated mass of the protein is only 30 kDa. Alternatively, the protein may form a dimer, perhaps around a single bound b-cyclodextrin ligand, which is not dissociated by boiling in the presence of SDS and a reducing agent.

The ANG portion forms disulphide-bonded polymeric species was demonstrated by native-PAGE of the copper-oxidised affinity purified proteins. The fusion protein has been demonstrated to contain the novel starch binding activity. Importantly, it is believed that the modified protein has not lost the ability to polymerise through the cysteine residues at the N- and C-termini and therefore the novel protein can be incorporated into the gluten macropolymer in wheat flour.

Demonstration of the capacity of the modified seed-storage protein with macromolecule-binding domain (in this instance ANG/SBD/Cys7Cys236) to form disulphide-bonded polymeric species (FIG. 19). This demonstrates the ability of the protein to be incorporated into the gluten macropolymer through disulphide bonds.

Table 1 demonstrates the identity between the molecular weights of the experimentally determined tryptic fragments of the major β-cyclodextrin-binding protein (starch-binding protein) purified from the ANG/SBD/Cys7Cys236 strain and the theoretical masses of the tryptic fragments of the ANG/SBD/Cys7Cys236 protein. The identification of the 30 kDa protein as an endogenous bacterial maltose-binding protein is also provided.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Aalen, R. B. 1995. The transcript encoding two oleosin isoforms are both present in the aleurone and in the embryo of barley (*Hordeum vulgare*) seeds. Plant Mol. Biol. 28:583–588

Bekes, F., Gras, P. W, and Gupta, R. B. 1994. Mixing properties as a measure of reversible reduction and oxidation of doughs. Cereal Chemistry 71:44–50

Bushuk, W. 1998. Interactions in wheat doughs. In Interactions: The keys to cereal quality. R. J. Hamer, R. C. Hoseney Eds. American Association of Cereal Chemists, Inc. St Paul, Minn, pp 1–16.

Chamberlain, D. A., Brettell, R. I. S., Last, D. I., Witrzens, B., McElroy, D., Dolferus, R., Dennis, E. S. 1994. The use of the EMu promoter with antibiotic and herbicide resistance genes for the selection of transgenic wheat callus and rice plants. Australian Journal of Plant Physiology. 21: 95–112.

Ciaffi, M., Lee, Y. K., Tamas, L., Gupta, R., Skerritt, J. and Appels, R. 1999. The low-molecular-weight glutenin subunit proteins of primitive wheats. III. The genes from D-genome species. Theoretical and Applied Genetics 98: 135–148.

Dubreil, L., Compoint, J-P, and Marion, D. 1997. Interaction of Puroindolines with wheat flour polar lipids determines their foaming properties. J. Agric. Food Chem. 45:108–116

Gan, Z., Ellis, P. R, and Schofield, J. D. 1995. Gas cell Stabilisation and gas retention in wheat bread dough. Journal of Cereal Science 21:215–230

Huang, A. H. C. 1996. Oleosins and oil bodies in seeds and other organs. Plant Physiology 110:1055–1061

Kasarda, D. D. 1989. Glutenin structure in relation to wheat quality. Pages 277–302 in: Wheat is unique. Y. Pomeranz, Ed. Amer, assoc. Cereal Chem., St Paul, Minn.

Kirschman, J. A, and Cramer, J. H. 1988. Two new tools: multi-purpose cloning vectors that carry kanamycin or spectinomycin/streptomycin resistance markers. Gene 68: 163–165.

Kobrehel, K. and Sauvaire, Y. 1990. Particular lipid composition in isolated proteins of durum wheat. J. Agric. Food Chem. 38:1164–1171

Laemmli, U. K. 1970. Cleavage of structural proteins during the assembly of the head of bacteriophage T4. Nature 227:680–685

Le Gal-Coeffet M-F., Jacks. A. J. Sorimachi. K. Williamson, M. P., Williamson. G. and Archer. D. B. 1995. Expression in *Aspergilus Niger* of the starch-binding-domain of glucoamylase. Eur. J. Biochem. 233.561–567

MacRitchie. F. 1992. Physicochemical properties of wheat proteins in relation to functionality. Adv. Food Nutr. Research 36:1–87

Morrison, W. R. 1989, Recent progress on the chemistry and functionality of flour lipids. Pages 131–149 in: Wheat end use properties: Wheat and flour characterisation for specific end-uses. H. Salovaara, Ed. University of Helsinki, Lahti.

Tamas, L., Bekes. F. Greenfield, J., Tatham, A. S. Gras, P. W. Shewry, P. R. and Appels, R. 1998. Heterologous expression and dough mixing studies of wild-type and mutant C hordeins. Journal of Cer. Science 27:15–22

Weeks, J. T. Anderson. O. D. and Blechl. A. E. 1993. Rapid production of multiple independent lines of fertile transgenic wheat (*Triticum aestivum*). Plant Physiology 102:1077–1084

Witrzens. B. Brettell. R. I. S., Murray, F. R. McElroy, D., Li. Z., Dennis. E. S. 1998. Comparison of three selectable marker genes for transformation of wheat by microprojectile bombardment. Australian Journal of Plant Physiology 25:39–44.

What is claimed is:

1. A method of producing a modified glutenin or seed-storage protein, the method comprising adding to a glutenin or seed-storage protein an exogenous amino acid sequence from a protein other than said glutenin or seed-storage protein which confers to the modified protein the ability to bind a ligand, wherein the modified protein has an ability to incorporate into gluten.

2. The method of claim 1 wherein the exogenous amino acid sequence includes one or more cysteine residues.

3. The method of claim 2 wherein one or more cysteine residues are incorporated at one or both ends of the amino acid sequence of the protein.

4. The method of claim 1 wherein the modified protein further comprises one or more exogenous amino acid residues which confer to the protein an enhanced ability to incorporate into gluten when compared to said glutenin or seed-storage protein.

5. The method of claim 1 wherein the exogenous amino acid sequence binds lipid or starch.

6. The method of claim 5 wherein the exogenous amino acid sequence that binds lipid is derived from barley oleosin protein or wheat $CM_{16}$ protein.

7. The method of claim 5 wherein the exogenous amino acid sequence that binds starch is derived from glucoamylase from *Aspergillus niger*.

8. The method of claim 1 wherein the glutenin or seed-storage protein is a low molecular weight glutenin, high molecular weight glutenin, gliadin, puroindoline, grain softness protein, friabilin, or Chloroform/Methanol-soluble protein.

9. The method of claim 8 wherein the glutenin or seed-storage protein is C hordein from barley.

10. A modified glutenin or seed-storage protein having an ability to incorporate into gluten, comprising an exogenous amino acid sequence which confers to the modified protein the ability to bind a ligand said modified protein being produced by the method of claim 1.

11. A modified glutenin or seed-storage protein having an ability to incorporate into gluten, comprising an exogenous amino acid sequence from a protein other than a corresponding unmodified glutenin or seed-storage protein which confers to the modified protein the ability to bind a ligand.

12. The modified glutenin or seed-storage protein of claim 11 wherein the exogenous amino acid sequence binds lipid or starch.

13. The modified glutenin or seed-storage protein of claim 12 wherein the exogenous amino acid sequence that binds lipid is derived from barley oleosin protein or wheat CM16 protein.

14. The modified glutenin or seed-storage protein of claim 12 wherein the exogenous amino acid sequence that binds starch is derived from glucoamylase from *Aspergillus niger*.

15. The modified glutenin or seed-storage protein of claim 11 wherein the unmodified glutenin or seed-storage protein is a low molecular weight glutenin, high molecular weight glutenin, gliadin, puroindoline, grain softness protein, friabilin, or Chloroform/Methanol-soluble protein.

16. A modified glutenin or seed-storage protein selected from the group consisting of ANG/SBD/Cys7Cys 236, ANG/OHBD/Cys7Cys236, and ANG/$CM_{16}$/Cys7Cys126.

* * * * *

SEQUENCE LISTING

<160> NUMBER OF SEQ ID NOS: 26

<210> SEQ ID NO 1
<211> LENGTH: 41
<212> TYPE: DNA
<213> ORGANISM: Artificial Sequence
<220> FEATURE:
<223> OTHER INFORMATION: unknown

<400> SEQUENCE: 1
gtcatgaggc aactaaaccc ttgcagccaa gagttgcaat c        41

<210> SEQ ID NO 2
<211> LENGTH: 51
<212> TYPE: DNA
<213> ORGANISM: Artificial Sequence
<220> FEATURE:
<223> OTHER INFORMATION: unknown

<400> SEQUENCE: 2
ggatccctag accatactcc atatgcatga agcttgttgg gggactggtt g        51

<210> SEQ ID NO 3
<211> LENGTH: 24
<212> TYPE: DNA
<213> ORGANISM: Artificial Sequence
<220> FEATURE:
<223> OTHER INFORMATION: unknown

<400> SEQUENCE: 3
caagcttgta ccactcccac cgcc        24

<210> SEQ ID NO 4
<211> LENGTH: 27
<212> TYPE: DNA
<213> ORGANISM: Artificial Sequence
<220> FEATURE:
<223> OTHER INFORMATION: unknown

<400> SEQUENCE: 4
ccatatgcac cgccaggtgt cagtcac                                27

<210> SEQ ID NO 5
<211> LENGTH: 21
<212> TYPE: DNA
<213> ORGANISM: Artificial Sequence
<220> FEATURE:
<223> OTHER INFORMATION: unknown

<400> SEQUENCE: 5
gtcggcaatg aagattgcac c                                      21

<210> SEQ ID NO 6
<211> LENGTH: 24
<212> TYPE: DNA
<213> ORGANISM: Artificial Sequence
<220> FEATURE:
<223> OTHER INFORMATION: unknown

<400> SEQUENCE: 6
tccaactgcg ttctcctctt ggcc                                   24

<210> SEQ ID NO 7
<211> LENGTH: 24
<212> TYPE: DNA
<213> ORGANISM: Artificial Sequence
<220> FEATURE:
<223> OTHER INFORMATION: unknown

<400> SEQUENCE: 7
ggatccctag ctccactgag actc                                   24

<210> SEQ ID NO 8
<211> LENGTH: 33
<212> TYPE: DNA
<213> ORGANISM: Artificial Sequence
<220> FEATURE:
<223> OTHER INFORMATION: unknown

<400> SEQUENCE: 8
tgcgctcaag ctttaggcaa tgaagattgc acc                         33

<210> SEQ ID NO 9
<211> LENGTH: 30
<212> TYPE: DNA
<213> ORGANISM: Artificial Sequence
<220> FEATURE:
<223> OTHER INFORMATION: unknown

<400> SEQUENCE: 9
catactccat atgcagctcc actgagactc                             30

<210> SEQ ID NO 10
<211> LENGTH: 24
<212> TYPE: DNA
<213> ORGANISM: Artificial Sequence
<220> FEATURE:
<223> OTHER INFORMATION: unknown

<400> SEQUENCE: 10
caagcttacg atgttgctgg cggg                                            24

<210> SEQ ID NO 11
<211> LENGTH: 29
<212> TYPE: DNA
<213> ORGANISM: Artificial Sequence
<220> FEATURE:
<223> OTHER INFORMATION: unknown

<400> SEQUENCE: 11
ccatatgcac cagtaatagc caatagtgc                                       29

<210> SEQ ID NO 12
<211> LENGTH: 23
<212> TYPE: DNA
<213> ORGANISM: Artificial Sequence
<220> FEATURE:
<223> OTHER INFORMATION: unknown

<400> SEQUENCE: 12
caaccatgtc ctgaaccttc acc                                             23

<210> SEQ ID NO 13
<211> LENGTH: 18
<212> TYPE: DNA
<213> ORGANISM: Artificial Sequence
<220> FEATURE:
<223> OTHER INFORMATION: unknown

<400> SEQUENCE: 13
tggctgttga ggttgcac                                                   18

<210> SEQ ID NO 14
<211> LENGTH: 140
<212> TYPE: DNA
<213> ORGANISM: Artificial Sequence
<220> FEATURE:
<223> OTHER INFORMATION: unknown

<400> SEQUENCE: 14
atagaataca gcatgctccc ggccgccatg gccgcgggat tgtcatgagg caactaaacc     60
cttgcagcgt cccccaacaa gcttcatgca tatggagtat ggtctaggga tccgggtacc    120
gagctcgaat tcgccctata                                                140

<210> SEQ ID NO 15
<211> LENGTH: 20
<212> TYPE: PRT
<213> ORGANISM: Artificial Sequence
<220> FEATURE:
<223> OTHER INFORMATION: unknown

<400> SEQUENCE: 15

Met Arg Gln Leu Asn Pro Cys Ser Val Pro Gln Gln Ala Ser Cys Ile
 1               5                  10                  15

Trp Ser Met Val
            20

<210> SEQ ID NO 16
<211> LENGTH: 243
<212> TYPE: DNA
<213> ORGANISM: Artificial Sequence
<220> FEATURE:

<223> OTHER INFORMATION: unknown

<400> SEQUENCE: 16

```
caagctttga aagccgctac tgcgacagca gctggatcat tgcttgtgct atccggacta      60
atactagctg gcacagtcat agcactcaca gtggccacac cagtgctagt catatttagc     120
ccagtgctag tgccagcggc catagcccta gcgctaatgt cagcaggctt tgtcacgtca     180
ggcgggctgg gcgtggctgc gctgagctcc tttagtgtgt tagccaatac tgcctgcata     240
tgg                                                                   243
```

<210> SEQ ID NO 17
<211> LENGTH: 81
<212> TYPE: PRT
<213> ORGANISM: Artificial Sequence
<220> FEATURE:
<223> OTHER INFORMATION: unknown

<400> SEQUENCE: 17

```
Gln Ala Leu Lys Ala Ala Thr Ala Thr Ala Ala Gly Ser Leu Leu Val
 1               5                  10                  15

Leu Ser Gly Leu Ile Leu Ala Gly Thr Val Ile Ala Leu Thr Val Ala
            20                  25                  30

Thr Pro Val Leu Val Ile Phe Ser Pro Val Leu Val Pro Ala Ala Ile
        35                  40                  45

Ala Leu Ala Leu Met Ser Ala Gly Phe Val Thr Ser Gly Gly Leu Gly
    50                  55                  60

Val Ala Ala Leu Ser Ser Phe Ser Val Leu Ala Asn Thr Ala Cys Ile
65                  70                  75                  80

Trp
```

<210> SEQ ID NO 18
<211> LENGTH: 477
<212> TYPE: DNA
<213> ORGANISM: Artificial Sequence
<220> FEATURE:
<223> OTHER INFORMATION: unknown

<400> SEQUENCE: 18

```
atgaggcaac taaccccttg cagccaagag ttgcaatcac cacaacaatc atatctgccg      60
cagccatatc cacaaaaccc atatctaccg caaaaaccat ttccagtgca gcaaccgttt     120
cacacacccc aacaatattt cccctatcta ccagaggaat tgtttcccca atatcaaata     180
ccaaccccccc tacaaccaca caaccattc ccccaacaac cacaacaacc tcttcctcgg    240
ccccaacaac cattcccctg gcaaccacaa caaccatttc cccagcccca agaaccaatt    300
ccccaacaac cattcccctg gcaaccacaa caaccatttc cccagcccca agaaccaatt    360
caacaaataa ttttccagca accccaacaa tcatacccctg tgcaacctca acagccattt    420
cctcaacaac ctcaaccagt cccccaacaa gcttcatgca tatggagtat ggtctag      477
```

<210> SEQ ID NO 19
<211> LENGTH: 158
<212> TYPE: PRT
<213> ORGANISM: Artificial Sequence
<220> FEATURE:
<223> OTHER INFORMATION: unknown

<400> SEQUENCE: 19

```
Met Arg Gln Leu Asn Pro Cys Ser Gln Glu Leu Gln Ser Pro Gln Gln
 1               5                  10                  15
```

```
Ser Tyr Leu Gln Gln Pro Tyr Pro Gln Asn Pro Tyr Leu Pro Gln Lys
             20                  25                  30

Pro Phe Pro Val Gln Gln Pro Phe His Thr Pro Gln Gln Tyr Phe Pro
         35                  40                  45

Tyr Leu Pro Glu Glu Leu Phe Pro Gln Tyr Gln Ile Pro Thr Pro Leu
     50                  55                  60

Gln Pro Gln Gln Pro Phe Pro Gln Gln Pro Gln Gln Pro Leu Pro Arg
 65                  70                  75                  80

Pro Gln Gln Pro Phe Pro Trp Gln Pro Gln Gln Pro Phe Pro Gln Pro
                 85                  90                  95

Gln Glu Pro Ile Pro Gln Gln Pro Gln Gln Pro Phe Pro Gln Gln Pro
             100                 105                 110

Gln Gln Pro Phe Pro Gln Gln Pro Gln Gln Ile Ile Phe Gln Gln Pro
         115                 120                 125

Gln Gln Ser Tyr Pro Val Gln Pro Gln Gln Pro Phe Pro Gln Gln Pro
     130                 135                 140

Gln Pro Val Pro Gln Gln Ala Ser Cys Ile Trp Ser Met Val
145                 150                 155

<210> SEQ ID NO 20
<211> LENGTH: 338
<212> TYPE: DNA
<213> ORGANISM: Aspergillus niger

<400> SEQUENCE: 20
aagcttctac cactcccacc gccgtggctg tgactttcga tctgacagct accaccacct      60
acggcgagaa catctacctg gtcggatcga tctctcagct gggtgactgg gaaaccagcg     120
acggcatagc tctgagtgct gacaagtaca cttccagcga cccgctctgg tatgtcactg     180
tgactctgcc ggctggtgag tcgtttgagt acaagtttat ccgcattgag agcgatgact     240
ccgtggagtg ggagagtgat cccaaccgag aatacaccgt tcctcaggcg tgcggaacgt     300
cgaccgcgac ggtgactgac acctggcggt gcatatgg                             338

<210> SEQ ID NO 21
<211> LENGTH: 112
<212> TYPE: PRT
<213> ORGANISM: Aspergillus niger

<400> SEQUENCE: 21

Ala Ser Thr Thr Pro Thr Ala Val Ala Val Thr Phe Asp Leu Thr Ala
 1               5                  10                  15

Thr Thr Thr Tyr Gly Glu Asn Ile Tyr Leu Val Gly Ser Ile Ser Gln
             20                  25                  30

Leu Gly Asp Trp Glu Thr Ser Asp Gly Ile Ala Leu Ser Ala Asp Lys
         35                  40                  45

Tyr Thr Ser Ser Asp Pro Leu Trp Tyr Val Thr Val Thr Leu Pro Ala
     50                  55                  60

Gly Glu Ser Phe Glu Tyr Lys Phe Ile Arg Ile Glu Ser Asp Asp Ser
 65                  70                  75                  80

Val Glu Trp Glu Ser Asp Pro Asn Arg Glu Tyr Thr Val Pro Gln Ala
                 85                  90                  95

Cys Gly Thr Ser Thr Ala Thr Val Thr Asp Thr Trp Arg Cys Ile Trp
             100                 105                 110

<210> SEQ ID NO 22
```

-continued

```
<211> LENGTH: 371
<212> TYPE: DNA
<213> ORGANISM: Artificial Sequence
<220> FEATURE:
<223> OTHER INFORMATION: unknown

<400> SEQUENCE: 22
aagctttcgg caatgaagat tgcaccccat ggatgagtac tctgatcact ccactcccaa      60
gctgccgtga ctatgtggaa caacaagcat gtcgcatcga acgcccggg tcgccgtacc     120
tcgccaagca gcagtgctgt ggggagcttg caaacattcc gcagcagtgc cgatgccagg    180
cgctgcgcta cttcatgggg ccgaagtctc gtccggatca gagcggcctc atggaactcc    240
ccggatgccc tagggaggtg cagatggact tcgtgaggat actcgtcacg ccggggtact    300
gcaacttgac gaccgttcac aacactccgt actgcctcgc tatggaggag tctcagtgga    360
gctgcatatg g                                                         371

<210> SEQ ID NO 23
<211> LENGTH: 123
<212> TYPE: PRT
<213> ORGANISM: Artificial Sequence
<220> FEATURE:
<223> OTHER INFORMATION: unknown

<400> SEQUENCE: 23

Ala Ile Gly Asn Glu Asp Cys Thr Pro Trp Met Ser Thr Leu Ile Thr
  1               5                  10                  15

Pro Leu Pro Ser Cys Arg Asp Tyr Val Glu Gln Gln Ala Cys Arg Ile
             20                  25                  30

Glu Thr Pro Gly Ser Pro Tyr Leu Ala Lys Gln Gln Cys Cys Gly Glu
         35                  40                  45

Leu Ala Asn Ile Pro Gln Gln Cys Arg Cys Gln Ala Leu Arg Tyr Phe
     50                  55                  60

Met Gly Pro Lys Ser Arg Pro Asp Gln Ser Gly Leu Met Glu Leu Pro
 65                  70                  75                  80

Gly Cys Pro Arg Glu Val Gln Met Asp Phe Val Arg Ile Leu Val Thr
                 85                  90                  95

Pro Gly Tyr Cys Asn Leu Thr Thr Val His Asn Thr Pro Tyr Cys Leu
            100                 105                 110

Ala Met Glu Glu Ser Gln Trp Ser Cys Ile Trp
            115                 120

<210> SEQ ID NO 24
<211> LENGTH: 123
<212> TYPE: PRT
<213> ORGANISM: Artificial Sequence
<220> FEATURE:
<223> OTHER INFORMATION: unknown

<400> SEQUENCE: 24

Ala Ile Gly Asn Glu Asp Cys Thr Pro Trp Thr Ser Thr Leu Ile Thr
  1               5                  10                  15

Pro Leu Pro Ser Cys Arg Asn Tyr Val Glu Gln Gln Ala Cys Arg Ile
             20                  25                  30

Glu Met Pro Gly Pro Pro Tyr Leu Ala Lys Gln Glu Cys Cys Glu Gln
         35                  40                  45

Leu Ala Asn Ile Pro Gln Gln Cys Arg Cys Gln Ala Leu Arg Tyr Phe
     50                  55                  60

Met Gly Pro Lys Ser Arg Pro Asp Gln Ser Gly Leu Met Glu Leu Pro
```

```
                         65                  70                  75                  80
Gly Cys Pro Arg Glu Val Gln Met Asn Phe Val Pro Ile Leu Val Thr
                    85                  90                  95

Pro Gly Tyr Cys Asn Leu Thr Thr Val His Asn Thr Pro Tyr Cys Leu
                100                 105                 110

Gly Met Glu Glu Ser Gln Trp Ser Cys Ile Trp
        115                 120
```

<210> SEQ ID NO 25
<211> LENGTH: 377
<212> TYPE: DNA
<213> ORGANISM: wheat

<400> SEQUENCE: 25

```
aagcttacga tgttgctggc gggggtggtg ctcaacaatg ccctgtagag acaaagctaa      60
attcatgcag gaattacctg ctagatcgat gctcaacgat gaaggatttc ccggtcacct     120
ggcgttggtg gaaatggtgg aagggaggtt gtcaagagct ccttggggag tgttgcagtc     180
ggctcggcca aatgccaccg caatgccgct gcaacatcat ccagggggtca atccaaggcg    240
atctcggtgg catcttcgga tttcagcgtg atcgggcaag caaagtgata caagaagcca     300
agaacctgcc gcccaggtgc aaccagggcc ctccctgcaa catccccggc actattggct     360
attactggtg catatgg                                                    377
```

<210> SEQ ID NO 26
<211> LENGTH: 125
<212> TYPE: PRT
<213> ORGANISM: wheat

<400> SEQUENCE: 26

```
Ala Tyr Asp Val Ala Gly Gly Gly Ala Gln Gln Cys Pro Val Glu
 1               5                  10                  15

Thr Lys Leu Asn Ser Cys Arg Asn Tyr Leu Leu Asp Arg Cys Ser Thr
                20                  25                  30

Met Lys Asp Phe Pro Val Thr Trp Arg Trp Lys Trp Trp Lys Gly
            35                  40                  45

Gly Cys Gln Glu Leu Leu Gly Glu Cys Cys Ser Arg Leu Gly Gln Met
        50                  55                  60

Pro Pro Gln Cys Arg Cys Asn Ile Ile Gln Gly Ser Ile Gln Gly Asp
65                  70                  75                  80

Leu Gly Gly Ile Phe Gly Phe Gln Arg Asp Arg Ala Ser Lys Val Ile
                85                  90                  95

Gln Glu Ala Lys Asn Leu Pro Pro Arg Cys Asn Gln Gly Pro Pro Cys
                100                 105                 110

Asn Ile Pro Gly Thr Ile Gly Tyr Tyr Trp Cys Ile Trp
            115                 120                 125
```